(12) United States Patent
Garcia et al.

(10) Patent No.: US 9,884,309 B2
(45) Date of Patent: Feb. 6, 2018

(54) METAL-ORGANIC FRAMEWORKS

(71) Applicant: Cambridge Enterprise Limited, Cambridge (GB)

(72) Inventors: Jose De Jesus Velazquez Garcia, Cambridge (GB); Thomas Douglas Bennett, Cambridge (GB); David Fairen-Jimenez, Cambridge (GB); Tian Tian, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 0 days.

(21) Appl. No.: 15/317,380

(22) PCT Filed: Jun. 9, 2015

(86) PCT No.: PCT/GB2015/051688
§ 371 (c)(1),
(2) Date: Dec. 8, 2016

(87) PCT Pub. No.: WO2015/189599
PCT Pub. Date: Dec. 17, 2015

(65) Prior Publication Data
US 2017/0113205 A1    Apr. 27, 2017

(30) Foreign Application Priority Data

Jun. 10, 2014 (GB) .................................. 1410297.4
Dec. 17, 2014 (GB) .................................. 1422479.4

(51) Int. Cl.
*B01J 20/22* (2006.01)
*B01J 20/28* (2006.01)
*C07F 3/06* (2006.01)

(52) U.S. Cl.
CPC ......... *B01J 20/226* (2013.01); *B01J 20/2803* (2013.01); *B01J 20/2808* (2013.01); *B01J 20/28011* (2013.01); *B01J 20/28042* (2013.01); *B01J 20/28064* (2013.01); *B01J 20/28083* (2013.01); *B01J 20/28092* (2013.01); *C07F 3/06* (2013.01)

(58) Field of Classification Search
CPC ............................... B01J 20/22; B01J 20/226
USPC ........................................................ 502/401
See application file for complete search history.

(56) References Cited

U.S. PATENT DOCUMENTS

| | | | |
|---|---|---|---|
| 2009/0025556 A1 | 1/2009 | Mirkin et al. | |
| 2011/0010826 A1 | 1/2011 | Kaskel | |
| 2012/0055880 A1 | 3/2012 | Loiseau et al. | |
| 2013/0157837 A1 | 6/2013 | Banerjee et al. | |
| 2013/0197235 A1 | 8/2013 | Thompson et al. | |
| 2013/0283849 A1 | 10/2013 | Baumann et al. | |

FOREIGN PATENT DOCUMENTS

| | | |
|---|---|---|
| WO | 2003102000 | 12/2003 |
| WO | 2006050898 | 5/2006 |
| WO | 2011116222 | 9/2011 |
| WO | 2012020214 | 2/2012 |
| WO | 2013058844 | 4/2013 |

OTHER PUBLICATIONS

Tan et al., (2006) "Nucleation and growth characteristics of a binary low-mass organogel," Langmuir 22, 7416-7420.
Tian et al (2015) "Mechanically and chemically robust ZIF-8 monoliths with high volumetric adsorption capacity," Journals of Materials Chemistry A, 3: 2999-3005.
Tian et al., (2007) "Design and Generation of Extended Zeolitic Metal-Organic Frameworks (ZMOFs): Synthesis and Crystal Structures of Zinc(II) Imidazolate Polymers with Zeolitic Topologies," Chemistry, 13: 4146-54.
Wilmer et al.(2012) "Large-scale screening of hypothetical metal-organic frameworks," Nature Chemistry, 4: 83-89.
Zacharia et al., (2010) "Volumetric hydrogen sorption capacity of monoliths prepared by mechanical densification of MOF-177," Journal of Materials Chemistry, 20; 2145-2151.
Apetz & Bruggen (2003) "Transparent Alumina: A Light-Scattering Model," J. Am. Ceram. Soc. 86(3): 480-486.
Bennett et al., (2013) "Ball-Milling-Induced Amorphization of Zeolitic Imidazolate Frameworks (ZIFs) for the Irreversible Trapping of Iodine," Chemistry Eur. J., 19, 7049-7055.
Bundschuh et al. (2012) "Mechanical properties of metal-organic frameworks: An indentation study on epitaxial thin films," Appl. Phys. Lett., 101: 101910.
Cao et al. (2013) "Hierarchical bicontinuous porosity in metal-organic frameworks templated from functional block co-oligomer micelles," Chem. Sci. 4, 3573-3577.
Casco et al. (2015) "High-Pressure Methane Storage in Porous Materials: Are Carbon Materials in the Pole Position?" Chemistry of Materials 27: 959-964.
Chapman et al. (2009) "Pressure-Induced Amorphization and Porosity Modification in a Metal-Organic Framework," J. Am. Chem. Soc., 131, 17546-17547.
Dorcheh & Abbasi (2008) "Silica aerogel; synthesis, properties and characterization," J. Mater. Process. Technol. 199 (1-3): 10-26.
Eslava et al. (2013) "Metal-Organic Framework ZIF-8 Films as Low- κ Dielectrics in Microelectronics," Chem. Mater., 25, 27-33.
Fairen-Jimenez et al. (2006) "Surface area and microporosity of carbon aerogels from gas adsorption and small- and wide-angle X-ray scattering measurements," The Journal of Physical Chemistry B 110: 8681-8688.
Fairen-Jimenez et al. (2006) "Porosity and surface area of monolithic carbon aerogels prepared using alkaline carbonates and organic acids as polymerization catalysts," Carbon 44 (11): 2301-2307.

(Continued)

*Primary Examiner* — Edward Johnson
(74) *Attorney, Agent, or Firm* — Rudy J. Ng; Bozicevic, Field & Francis LLP

(57) ABSTRACT

A metal-organic framework (MOF) body that includes MOF crystallites adhered to each other via a MOF binder is provided. In one embodiment, the body consists of: MOF crystallites; a MOF binder which binds the crystallites together in the body; optionally, residual solvent; and optionally, one or more additives, where the additives are present at a level of not more than 10% by mass. The MOF binder may have substantially the same composition as the MOF crystallites. Alternatively, the MOF binder may have a different composition to the MOF crystallites.

18 Claims, 29 Drawing Sheets

(56) References Cited

OTHER PUBLICATIONS

Fairen-Jimenez et al. (2008) "Inter-and intra-primary-particle structure of monolithic carbon aerogels obtained with varying solvents," Langmuir 24: 2820-2825.

Fairen-Jimenez et al. (2011) "Opening the Gate: Framework Flexibility in ZIF-8 Explored by Experiments and Simulations," J. Am. Chem. Soc., 133: 8900-8902.

Fairen-Jimenez et al. (2012)"Understanding excess uptake maxima for hydrogen adsorption isotherms in frameworks with rht topology," Chem. Commun. 48: 10496-10498.

Fairen-Jimenez et al (2012) "Flexibility and swing effect on the adsorption of energy-related gases on ZIF-8: combined experimental and simulation study," Dalton Transactions Issue 41 10752-10762.

Fu et al., (2013) "Incorporation of metal-organic framework UiO-66 into porous polymer monoliths to enhance the liquid chromatographic separation of small molecules," Chem. Commun., 49, 7162-7164.

Furukawa et al. (2013) "The Chemistry and Applications of Metal-Organic Frameworks," Science 341, 1230444-1230444-12.

Gandara et al. (2014) "High Methane Storage Capacity in Aluminum Metal-Organic Frameworks," J. Am. Chem Soc. 136(14): 5271-5274.

Getzschmann et al.(2010) "Methane storage mechanism in the metal-organic frameworkCu3(btc)2: An in situ neutron diffraction study," Microporous and Mesoporous Materials 136 (1-3): 50-58.

Gomez-Gualdron et al. (2014) "Exploring the limits of methane storage and delivery in nanoporous materials," The Journal of Physical Chemistry C 118(13): 6941-6951.

Gomez-Gualdron et al. (2016) "Application of Consistency Criteria to Calculate BET Areas of Micro- and Mesoporous Metal-Organic Frameworks," J. Am. Chem Soc. 138(1): 215-224.

He et al. (2014) "Methane storage in metal-organic frameworks," Chem. Soc. Rev. 43, 5657-5678.

Horcajada et al. (2009)"Colloidal route for preparing optical thin films of nanoporous metal-organic frameworks," Adv. Mater. 21(19): 1931-1935.

Huang et al. (2013) "Metal organic framework-organic polymer monolith stationary phases for capillary electrochromatography and nano-liquid chromatography," Analytica Chimica Acta 779: 96-103.

Jasuja et al. (2015) "Evaluation of MOFs for air purification and air quality control applications: Ammonia removal from air," Chemical Engineering Science, Elsevier 124(3): 118-124.

Juan-Juan et al. (2010) "A comparison of hydrogen storage in activated carbons and a metal-organic framework (MOF-5)," Carbon, 48(10): 2906-2909.

Kim et al. (2013) "High-rate synthesis of Cu—BTC metal-organic frameworks," Chem. Commun. 49, 11518-11520.

Küsgens et al.(2010) "Metal-Organic Frameworks in Monolithic Structure," J. Am. Ceram. Soc., 93(9): 2476-2479.

Katz et al. (2013) "A facile synthesis of UiO-66, UiO-67 and their derivatives," Chem. Commun. 49: 9449-9451.

Khan et al. (2011) "Facile synthesis of nano-sized metal-organic frameworks, chromium-benzenedicarboxylate, MIL-101." Chemical Engineering Journal 16: 1152-1157.

Li et al. (2013) "A synthetic route to ultralight hierarchically micro/mesoporous AI (III)-carboxylate metal-organic aerogels," Nature communications 4, 1774.

Liang et al. (2009) "Comparison of Cu-BTC and zeolite 13X for adsorbent based CO2 separation," Energy Procedia 1(1): 1265-1271.

Llewellyn et al. (2008) "High Uptakes of CO2 and CH4 in Mesoporous Metal-Organic Frameworks MIL-100 and MIL-101," Langmuir 24: 7245-7250.

Lohe et al., (2009) "Metal-organic framework (MOF) aerogels with high micro- and macroporosity," Chem. Commun. 6056-6058.

Makal et al. (2012) "Methane storage in advanced porous materials," Chem. Soc. Rev. 41, 7761-7779.

Marco-Lozar (2012) "MOF-5 and activated carbons as adsorbents for gas storage," International Journal of Hydrogen Energy 37(3) 2370-2381.

Mason et al. (2014). "Evaluating metal-organic frameworks for natural gas storage," Chemical Science 5, 32-51.

Millward & Yaghi (2005) "Metal-Organic Frameworks with Exceptionally High Capacity for Storage of Carbon Dioxide at Room Temperature," J. Am. Chem Soc. 127(51): 17998-17999.

Oliver & Pharr (2004) "Measurement of hardness and elastic modulus by instrumented indentation: Advances in understanding and refinements to methodology," J Mater Res, 19(1): 3-20.

Park et al, (2006) "Exceptional chemical and thermal stability of zeolitic imidazolate frameworks," Proc. Natl. Acad. Sci. 103(27): 10186-10191.

Pekala et al. (1989) "Organic aerogels from the polycondensation of resorcinol with formaldehyde," Journal of Materials Science 24: 3221-3227.

Peng et al. (2013) "Methane storage in metal-organic frameworks: current records, surprise findings, and challenges," J. Am. Chem. Soc. 135(32): 11887-11894.

Rouquerol et al, (1994) Recommendations for the Characterization of Porous Solids International Union Pure and Applied Chemistry, 66(8) 1739-1758.

Ryder et al. (2016) "Discovering connections between terahertz vibrations and elasticity underpinning the collective dynamics of the HKUST-1 metal-organic framework," J. CrystEngComm 18: 4303-4312.

Shieh et al. (2013) "Water-Based Synthesis of Zeolitic Imidazolate Framework-90 (ZIF-90) with a Controllable Particle Size," Chem. Eur. J. 19: 11139-11142.

Simon et al. (2015) "The materials genome in action: identifying the performance limits for methane storage," Energy & Environmental Science 8: 1190-1199.

Sing (1982) "Reporting Physisorption Data for Gas/Solid Systems," Pure & Appl. Chem., 54, 11, 2201-2218.

Song et al. (2012) "Zeolitic imidazolate framework (ZIF-8) based polymernanocomposite membranes for gas separation," Energy Environ. Sci., 5: 8359-8369.

Tabor et al., (1996) "Indentation hardness: Fifty years on a personal view," J. Philosophical Magazine A 74(5) 1207-1212.

Tan et al. (2010) "Chemical structure, network topology, and porosity effects on the mechanical properties of Zeolitic Imidazolate Frameworks," PNAS 107(22): 9938-9943.

Tan et al.(2009) "Anisotropic mechanical properties of polymorphic hybrid inorganic-organic framework materials with different dimensionalities," Acta Materialia, Elsevier 57(12): 3481-3496.

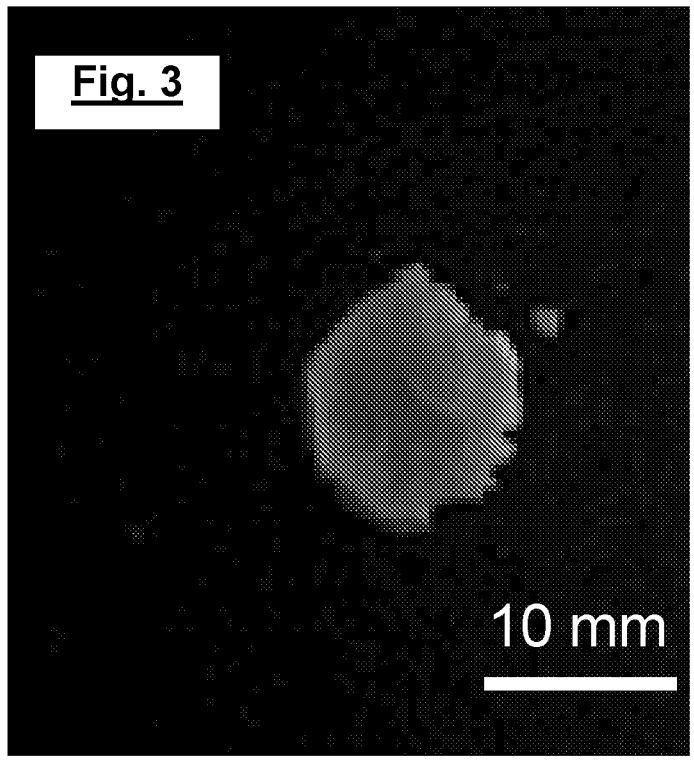
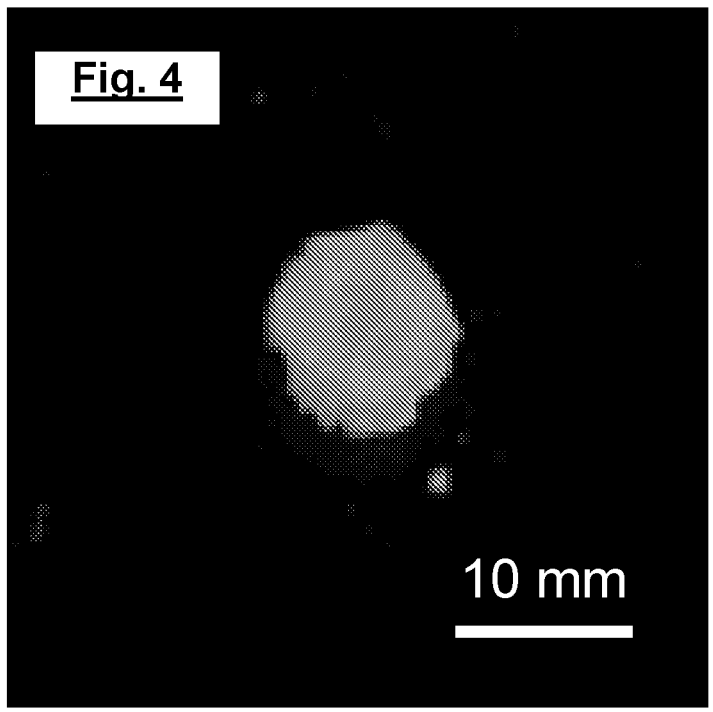

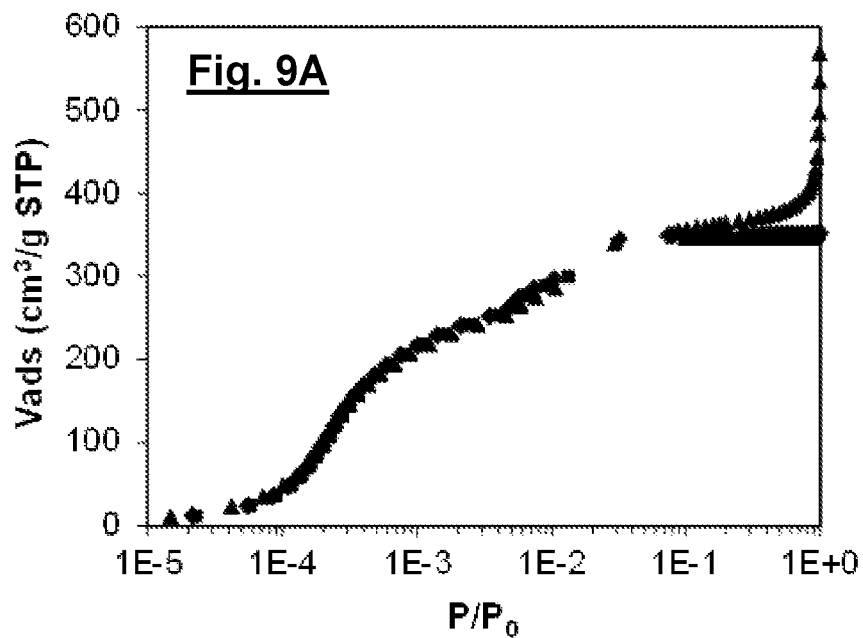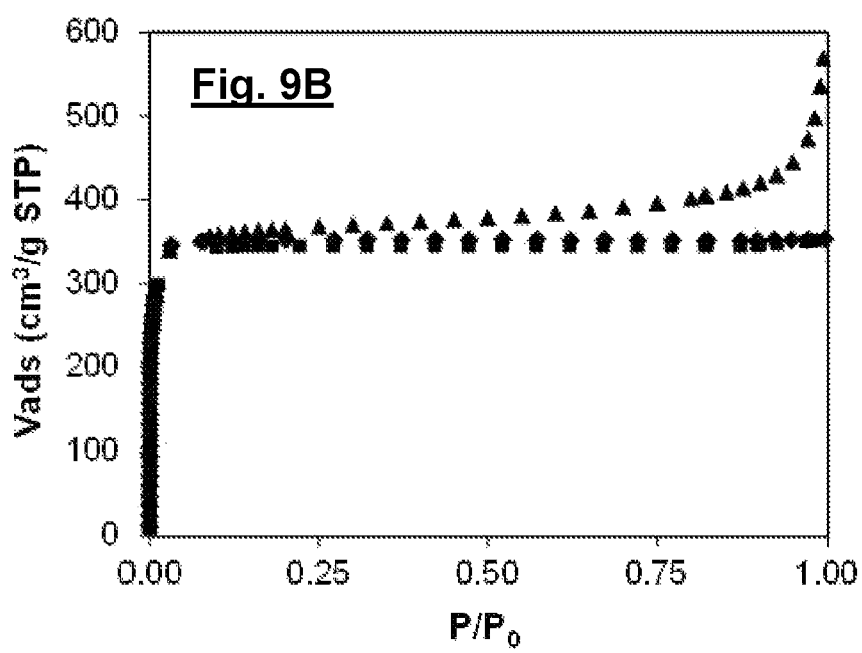

METAL-ORGANIC FRAMEWORKS

BACKGROUND TO THE INVENTION

Field of the Invention

The present invention relates to metal-organic framework (MOF) materials and to methods for their manufacture. The invention has particular, but not exclusive, applicability to monolithic forms of the materials. These are of interest for various applications, including gas adsorption applications.

Related Art

Metal-organic frameworks (MOFs) are porous crystalline materials prepared by the self-assembly of metal ions and organic ligands. MOFs can have large pore volumes and apparent surface areas as high as 8,000 $m^2$/g. MOFs combine a structural and chemical diversity that make them attractive for many potential applications, including gas storage, gas separation and purification, sensing, catalysis and drug delivery. The most striking advantage of MOFs over more traditional porous materials is the possibility to tune the host/guest interaction by choosing the appropriate building blocks, i.e. the metal ions and organic ligands, from which the MOF is formed.

WO 2010/148463 discloses a method for synthesis of MOFs in which the synthesis conditions are mild—typically below 30° C.—and the synthesis proceeds relatively quickly—typically in less than 1 hour. The synthesis takes place in a mixture of water and ethanol. The material studied in WO 2010/148463 is $Cu_3(BTC)_2$-type MOF.

Fu et al (2013) reports on efforts to incorporate a MOF (UiO-66) into a copolymer (MAA-co-EDMA) matrix, for use in liquid chromatography. The resulting structure is described as a "monolith", and comparisons are made with a monolith formed using the copolymer only. SEM analysis shows that the microstructure of the material includes spherical MOF particles which adhere to the copolymer matrix. Huang et al (2013) provides similar disclosure.

US 2010/0181212 discloses MOF materials supported on open cell polymer foam structures, for use in gas storage applications.

Küsgens et al (2010) discloses the manufacture of $Cu_3(BTC)_2$ MOF material in situ on cordierite monolithic honeycomb structures. The results are reported to be poor. Additionally, Küsgens et al (2010) discloses the manufacture of $Cu_3(BTC)_2$-based honeycomb structures, formed by mixing $Cu_3(BTC)_2$ powder with a silicone-based binder and a methyl hydroxyl propyl cellulose plasticizer. The structures were formed by extrusion and subsequent drying at 120° C.

SUMMARY OF THE INVENTION

The present inventors consider that one of the main challenges for the industrial use of MOFs is to prepare them in a suitable shape for a given application, in order to translate advantageous properties of the materials into industrial products. During the synthesis processes used to date in the art, MOFs are generally obtained in a powdered crystalline state. This makes them costly to shape for final industrial applications. Furthermore, the use of binders and high pressure processes to pelletize the material in order to create suitable monolithic structures causes significant reductions of the porous properties (e.g. the BET surface area per unit volume and/or the degree of microporosity) of the material. Porous properties may be reduced due to collapses in the porosity when using high pressures, pore blocking caused by the binder preventing access to the porosity, and/or the presence of the binder reducing the final gravimetric amount of adsorbent in the pellet. In addition, pellets may present low densities of MOF due to the presence of interstitial spaces between the powdered crystallites of MOF, causing low volumetric adsorption capacities, as well as reduced mechanical properties compared to the MOF single crystal.

The present invention has been devised in order to address at least one of the above problems. Preferably, the present invention reduces, ameliorates, avoids or overcomes at least one of the above problems.

Accordingly, in a first preferred aspect, the present invention provides a metal-organic framework (MOF) monolith having a volume of at least 10 $mm^3$, wherein:

(i) when the monolith is formed from a composition capable of forming a MOF single crystal of the same composition, the BET surface area per unit bulk volume of the monolith is at least 0.6 times the BET surface area per unit bulk volume of said MOF single crystal of the same composition; and (ii) when the monolith is formed from a composition not capable of forming a single crystal of the same composition, instead being capable of forming a MOF single crystal and one or more remaining components of the composition, the BET surface area per unit bulk volume of the monolith is at least 0.6 times the volumetric weighted arithmetic mean of the BET surface area per unit bulk volume of said MOF single crystal and said remaining components, and wherein the BET surface area per unit bulk volume is determined based on the $N_2$ adsorption isotherm at 77K.

Certain optional features of the first aspect of the invention are now set out. These may be applied singly or in any combination, unless the context demands otherwise. These may also be applied, in any combination unless the context demands otherwise, to any other aspect of the invention.

Preferably, the monolith has a BET surface area per unit bulk volume of at least 0.7 times, 0.8 times or 0.9 times (i) the BET surface area per unit bulk volume of the MOF single crystal of the same composition or (ii) the volumetric weighted arithmetic mean of the BET surface area per unit bulk volume of said MOF single crystal and said remaining components.

Where necessary, the BET surface area per unit bulk volume of a MOF single crystal can alternatively be determined by calculation based on knowledge of the crystal structure and the micro-pores entrained in that crystal structure. The single crystal is therefore considered to be free of meso- and macro-pores.

Preferably, the BET surface area per unit bulk volume of the monolith is at least 600 $m^2$/$cm^3$.

The volume of the monolith (or body) may in some cases be smaller than 10 $mm^3$. For example, the volume of the monolith may be at least 1 $mm^3$, more preferably at least 2 $mm^3$, more preferably at least 3 $mm^3$, more preferably at least 4 $mm^3$, more preferably at least 5 $mm^3$.

In a second preferred aspect, the present invention provides a metal-organic framework (MOF) monolith having a volume of at least 10 $mm^3$ wherein the BET surface area per unit bulk volume of the monolith is at least 600 $m^2$/$cm^3$, wherein the BET surface area per unit bulk volume is determined based on the $N_2$ adsorption isotherm at 77K.

The volume of the monolith (or body) may in some cases be smaller than 10 $mm^3$. For example, the volume of the monolith may be at least 1 $mm^3$, more preferably at least 2 $mm^3$, more preferably at least 3 $mm^3$, more preferably at least 4 $mm^3$, more preferably at least 5 $mm^3$.

In describing some aspects and embodiments of the present invention, and comparative materials, it is useful to present values for porosity in terms of volume percent (vol %). This represents the ratio of the total volume of the pores (sometimes within a defined size range) to the volume of the monolith. It is possible to measure the bulk volume of a monolith by the Archimedes method in a mercury porosimeter, i.e. by determining the volume of mercury displaced by the monolith before allowing the mercury to infiltrate the pores of the monolith.

In a third preferred aspect, the present invention provides a metal-organic framework (MOF) monolith having a volume of at least 10 mm$^3$, the monolith having a meso-porosity of at most 10 vol %, wherein meso-porosity is defined as pores with diameter in the range 2-50 nm (macro-porosity being defined as pores of greater than 50 nm diameter), the porosity and pore size distributions being determined based on the $N_2$ adsorption isotherm at 77K.

The volume of the monolith (or body) may in some cases be smaller than 10 mm$^3$. For example, the volume of the monolith may be at least 1 mm$^3$, more preferably at least 2 mm$^3$, more preferably at least 3 mm$^3$, more preferably at least 4 mm$^3$, more preferably at least 5 mm$^3$.

It is at present considered that the determination of porosity and pore size distributions based on the $N_2$ adsorption isotherm at 77K is suitable for determination of micro- and meso-porosity for MOF materials. Determination of porosity and pore size distributions over 50 nm, i.e. macro-porosity, may be carried out by alternative methods, such as mercury porosimetry.

Preferably, the MOF monolith has a micro-porosity, defined as pores with diameter less than 2 nm, of at least 40 vol %. More preferably, the MOF monolith has a micro-porosity of at least 50 vol %, still more preferably at least 55 vol % and still more preferably at least 60 vol %.

In a fourth preferred aspect, the present invention provides a metal-organic framework (MOF) monolith having a volume of at least 10 mm$^3$, wherein:
(i) when the monolith is formed from a composition capable of forming a MOF single crystal of the same composition, the monolith has a micro-porosity, defined as pores with diameter less than 2 nm, of at least 0.6 times the micro-porosity of a MOF single crystal of the same composition; and
(ii) when the monolith is formed from a composition not capable of forming a single crystal of the same composition, instead being capable of forming a MOF single crystal and one or more remaining components of the composition, the monolith has a micro-porosity of at least 0.6 times the volumetric weighted arithmetic mean of the micro-porosity of said MOF single crystal and said remaining components, and wherein the porosity and pore size distributions are determined based on the $N_2$ adsorption isotherm at 77K.

The delimitation of micro-porosity, meso-porosity and macro-porosity is as follows:
Micro-porosity: pore sizes below 2 nm
Meso-porosity: pore sizes in the range 2-50 nm
Macro-porosity: pore sizes larger than 50 nm This approach follows that of IUPAC and is applicable to porous materials, including MOF materials [Rouquerol et al (1994) and Sing (1982)].

Where necessary, the micro-porosity of a MOF single crystal can alternatively be determined by calculation based on knowledge of the crystal structure and the micro-pores entrained in that crystal structure. The single crystal is therefore considered to be free of meso- and macro-pores.

Preferably, the monolith has a micro-porosity of at least 0.7 times, 0.8 times or 0.9 times (i) the micro-porosity of the MOF single crystal of the same composition or (ii) the volumetric weighted arithmetic mean of the micro-porosity of said MOF single crystal and said remaining components.

Preferably, the density of the MOF monolith is at least 90% of (i) the density of the MOF single crystal of the same composition or (ii) the volumetric weighted arithmetic mean of the density of said MOF single crystal and said remaining components. In this case, the density of the MOF single crystal of the same composition can be determined by calculation based on knowledge of the crystal structure. The single crystal is considered to be free of meso- and macro-pores. More preferably, the MOF monolith has a density of at least 95%, more preferably at least 100%, more preferably at least 105% or more preferably at least 110% of the density of (i) the MOF single crystal of the same composition or (ii) the volumetric weighted arithmetic mean of the density of said MOF single crystal and said remaining components.

In some embodiments, it is preferred for the monolith to have as low a value for the meso- and macro-porosity as possible. For example the cumulative meso- and macro-porosity may be less than 1 vol %. This is advantageous where the intended application of the material is as an adsorbent material, e.g., for gases such as $CO_2$, $H_2$, $CH_4$, etc., where the development of high micro-pore volumes allows the adsorption of greater amounts of the relevant gas.

However, in some embodiments, it is preferred for the monolith to have some meso- and/or macro-porosity, in order to promote flow through the monolith. In these circumstances, the meso- and macro-pores provide flow passages to the micro-pores. Whether this is wanted again depends on the intended application of the material, the advantage of improved transport through the monolith being balanced against lower available surface area for adsorption due to proportionally smaller amount of micro-porosity per unit volume. Meso- and/or macro-porosity can be included in the monolith by the use of additives in the manufacturing process. Deliberate hierarchical porosity of this type can provide a useful balance in the properties of the monoliths for particular applications which require flow through the monolith.

For example, the monolith can be produced using a template material, in and/or around which the monolith is allowed to form. The template material can subsequently be removed to leave a suitable network of porosity through the monolith. The network of porosity can be meso- and/or macro-scale porosity. Suitable bi-continuous porosity can be formed in the context of MOFs as reported in Cao et al (2013).

Using $N_2$ adsorption at 77K, it is possible to measure micro- and meso-porosity. Typically, the micro-pore volume is obtained at relative pressure $P/P_0=0.1$, whereas adsorption at higher pressures is related to meso-porosity until $P/P_0=0.98$.

Mercury porosimetry can be used to measure the "bulk" density of the monolith since Hg does not penetrate any porosity at atmospheric pressure. In an alternative arrangement, mercury porosimetry can also be used to measure macro and meso-porosity, by increasing the Hg pressure and measuring the extent of intrusion of Hg into the pores of the monolith with pressure. Mercury porosimetry cannot be used to measure the micro-porosity.

Some work reported for comparison purposes relates to powder materials. In this case, the bulk density is the tap bulk density, i.e. the apparent density of a powder based on causing a sample of the powder to settle in a receptacle by tapping, measuring the mass and dividing this by the apparent volume of the sample. For MOF materials in powder form, this therefore includes the volume occupied by micro-, meso- and macro-porosity and also interstitial spaces between the powder particles.

The volume of the monolith (or body) may in some cases be smaller than 10 $mm^3$. For example, the volume of the monolith may be at least 1 $mm^3$, more preferably at least 2 $mm^3$, more preferably at least 3 $mm^3$, more preferably at least 4 $mm^3$, more preferably at least 5 $mm^3$.

Preferably, the monolith has a volume of at least 50 $mm^3$, more preferably at least 100 $mm^3$, more preferably at least 500 $mm^3$, still more preferably at least 1000 $mm^3$. The term "monolith" is intended to include self-supporting bodies. It is intended to exclude forms of material that are formed on a substrate or other support, or which rely on another structure to be supported.

Preferably, the MOF monolith or body has a smallest linear dimension of at least 1 mm. That is, assuming that the monolith is not perfectly spherical, the shortest straight line passing through the material of the monolith has a length in the monolith of at least 1 mm. This dimension may be considered to be the thickness of the monolith, depending on the overall shape of the monolith. More preferably, the MOF monolith has a smallest linear dimension of at least 5 mm.

The monolith may comprise a composite material comprising particles of a first MOF composition in a matrix of a second MOF composition, as explained further below in relation to an independent aspect of the invention.

In a fifth preferred aspect, the present invention provides a metal-organic framework (MOF) monolith having a volume of at least 10 $mm^3$ which is substantially transparent.

A transparent MOF material is of particular use in spectroscopic gas analysis applications.

The volume of the monolith (or body) may in some cases be smaller than 10 $mm^3$. For example, the volume of the monolith may be at least 1 $mm^3$, more preferably at least 2 $mm^3$, more preferably at least 3 $mm^3$, more preferably at least 4 $mm^3$, more preferably at least 5 $mm^3$, In a sixth preferred aspect, the present invention provides a metal-organic framework (MOF) monolith having a volume of at least 10 $mm^3$ wherein the material of the monolith provides an in-line transmission of light at 645 nm through a material thickness of 0.8 mm of at least 10%.

Preferably, the in-line transmission is measured as set out in Apetz and van Bruggen (2003) and uses a laser source operating at 645 nm. Samples are ground and polished to a thickness of 0.8 mm to eliminate surface scattering. Light transmitted through the sample is detected at a detector, the detector being sized and located relative to the sample and light source such that light scattered at an angle of greater than 0.5° off axis is not detected. The in-line transmission is determined as the ratio of intensity of the light detected with the sample in position between the light source and the detector and with the sample absent.

Preferably, the material of the monolith provides an in-line transmission of light at 645 nm through a material thickness of 0.8 mm of at least 20%, at least 30%, at least 40%, at least 50%, at least 60%, at least 70% or at least 80%.

The volume of the monolith (or body) may in some cases be smaller than 10 $mm^3$. For example, the volume of the monolith may be at least 1 $mm^3$, more preferably at least 2 $mm^3$, more preferably at least 3 $mm^3$, more preferably at least 4 $mm^3$, more preferably at least 5 $mm^3$, In a seventh preferred aspect, the present invention provides a metal-organic framework (MOF) body comprising MOF crystallites adhered to each other via a MOF binder.

Preferably, the MOF body is a monolith. Preferably the body has a volume of at least 10 $mm^3$. Further preferred ranges for the volume of the body are set out above in relation to the monolith. For example, the volume of the monolith (or body) may in some cases be smaller than 10 $mm^3$. For example, the volume of the monolith may be at least 1 $mm^3$, more preferably at least 2 $mm^3$, more preferably at least 3 $mm^3$, more preferably at least 4 $mm^3$, more preferably at least 5 $mm^3$, Alternatively, the MOF body is a layer formed on a substrate. The nature of the substrate is not particularly limited. In the case where the intended application of the layer is based on substantial transparency of the layer, preferably the substrate is transparent or substantially transparent.

The crystallites typically have different orientation to each other. For example, the crystallites may be substantially randomly oriented.

The MOF binder preferably has substantially the same composition as the MOF crystallites. However, the MOF binder may have a different porosity or pore size distribution to the MOF crystallites. The MOF binder may have a lower degree of crystallization than the MOF crystallites. For example, the MOF binder may be substantially amorphous.

Alternatively, the MOF binder may have a different composition to the MOF crystallites. In that case, the MOF body may be formed of a composite MOF material.

In an eighth preferred aspect, the present invention provides a metal-organic framework (MOF) body consisting of:
MOF crystallites;
a MOF binder which binds the crystallites together in the monolith;
optionally, residual solvent; and
optionally, one or more additives, wherein the additives are present at a level of not more than 10% by mass.

Optional features set out with respect to the seventh aspect are applicable also to the eighth aspect.

Preferably, if present, the additives are present at a level of not more than 5% by mass, more preferably not more than 3% by mass, more preferably not more than 2% by mass, still more preferably not more than 1% by mass. It is permitted for unavoidable impurities to be present in the body.

Preferably, if present, the residual solvent is present at a level of not more than 5% by mass, more preferably not more than 3% by mass, more preferably not more than 2% by mass, still more preferably not more than 1% by mass.

Preferably, the MOF body is a monolith. Preferably the body has a volume of at least 10 $mm^3$. Further preferred ranges for the volume of the body are set out above in relation to the monolith. For example, the volume of the monolith (or body) may in some cases be smaller than 10 $mm^3$. For example, the volume of the monolith may be at least 1 $mm^3$, more preferably at least 2 $mm^3$, more preferably at least 3 $mm^3$, more preferably at least 4 $mm^3$, more preferably at least 5 $mm^3$, The crystallites typically have different orientation to each other. For example, the crystallites may be substantially randomly oriented.

The MOF binder preferably has substantially the same composition as the MOF crystallites. However, the MOF binder may have a different porosity or pore size distribution to the MOF crystallites. The MOF binder may have a lower degree of crystallization than the MOF crystallites. For example, the MOF binder may be substantially amorphous.

Alternatively, the MOF binder may have a different composition to the MOF crystallites. In that case, the MOF body may be formed of a composite MOF material.

In a ninth preferred aspect, the present invention provides a metal-organic framework (MOF) monolith, or a MOF layer formed on a substrate, wherein:

(i) when the monolith or layer is formed from a composition capable of forming a MOF single crystal of the same composition, the monolith has a Young's modulus, and/or hardness, measured via nanoindentation, greater than the Young's modulus and/or hardness of a MOF single crystal of the same composition; and (ii) when the monolith or layer is formed from a composition not capable of forming a single crystal of the same composition, instead being capable of forming a MOF single crystal and one or more remaining components of the composition, the monolith has a Young's modulus, and/or hardness, measured via nanoindentation, greater than the volumetric weighted arithmetic mean of the Young's modulus and/or hardness of said MOF single crystal and said remaining components.

Where (ii) applies, the monolith or layer may comprise a composite material comprising particles of a first MOF composition in a matrix of a second MOF composition.

The monolith may have a volume of at least 10 $mm^3$, for example, or another preferred range of volume as set out above. For example, the volume of the monolith (or body) may in some cases be smaller than 10 $mm^3$. For example, the volume of the monolith may be at least 1 $mm^3$, more preferably at least 2 $mm^3$, more preferably at least 3 $mm^3$, more preferably at least 4 $mm^3$, more preferably at least 5 $mm^3$, The Young's modulus (used here interchangeably with the term "elastic modulus"), and/or hardness, may be at least 1.05 times, more preferably at least 1.5 times or at least 2 times (i) the Young's modulus and/or hardness of the MOF single crystal of the same composition or (ii) the volumetric weighted arithmetic mean of the Young's modulus and/or hardness of the MOF single crystal and said remaining components.

In a tenth preferred aspect, the present invention provides a population of monoliths or bodies according to any one of the first to ninth aspects.

Such a population is of use in various applications. For example, the monoliths may be of substantially similar shape and/or dimensions. They may be used in a column arrangement with the spaces between them allowing for fluid (e.g. gas) flow. This is useful for gas separation applications. The number of monoliths in the population is not particularly limited, but as an example the number of monoliths may be at least 10, or at least 50, or at least 100.

In an eleventh preferred aspect, the present invention provides a process for manufacturing a metal-organic framework (MOF) monolith, or a MOF layer formed on a substrate, wherein the process includes the steps:

allowing the reaction of MOF precursors in a solvent to form the MOF composition; and forming a monolith or layer of the MOF composition including a drying stage to remove at least some of the solvent with a maximum temperature during the drying stage of not more than 50° C.

The process may include a step of concentration of particles of the MOF composition into a concentrate of the particles and solvent. This step may be carried out, for example, by centrifugation.

The maximum temperature during the drying stage is preferably not more than 40° C., more preferably not more than 30° C.

Preferably, the monolith is formed into a desired shape by the drying stage taking place with the material in a mould. The drying material then preferably conforms to the shape of the mould.

In a twelfth preferred aspect, the present invention provides a process for manufacturing a metal-organic framework (MOF) body, wherein the process includes the steps:

allowing the reaction of MOF precursors in a solvent to form the MOF composition;

concentration of particles of the MOF composition into a concentrate of the particles and solvent;

addition of additional MOF precursors to the concentrate; and forming a body of the MOF composition including a drying stage to remove at least some of the solvent with a maximum temperature during the drying stage of not more than 50° C.

Preferably, the MOF body is a MOF monolith. Alternatively the MOF body is a MOF layer formed on a substrate.

The step of concentrating the particles of the MOF composition into a concentrate of the particles and solvent may be carried out, for example, by centrifugation.

The maximum temperature during the drying stage is preferably not more than 40° C., more preferably not more than 30° C.

Preferably, the body is formed into a desired shape by the drying stage taking place with the material in a mould. The drying material then preferably conforms to the shape of the mould.

In a thirteenth preferred aspect, the present invention provides a process for manufacturing a metal-organic framework (MOF) body, wherein the process includes the steps:

providing particles of a first MOF composition;

addition of MOF precursors, corresponding to a second MOF composition, to the particles of the first MOF composition; and forming a composite MOF body comprising said particles of said first MOF composition in a matrix of the second MOF composition.

Preferably, the MOF body is a MOF monolith. Alternatively the MOF body is a MOF layer formed on a substrate.

The present invention is considered to have broad applicability to MOFs. Suitable MOF compositions for use with the present invention are:

ZIFs, such as ZIF-4, ZIF-8, ZIF-90, ZIF-zni;
UiO-Frameworks, such as UiO-66, UiO-67, UiO-68;
HKUST-1;
MIL-47, MIL-53.

In the case of a composite MOF material, the first MOF composition may be any of the MOF compositions listed above and the second MOF composition may be any other of the MOF compositions listed above.

Further optional features of the invention are set out below.

BRIEF DESCRIPTION OF THE DRAWINGS

Embodiments of the invention will now be described by way of example with reference to the accompanying drawings in which:

FIGS. 1-4 show optical micrographs of various materials:
FIG. 1 shows ZIF-8-HT.
FIG. 2 shows ZIF-8-LT.
FIG. 3 shows ZIF-8-ER under normal illumination and
FIG. 4 shows ZIF-8-ER under 365 nm UV light.

FIGS. 9A and 9B shows results of $N_2$ adsorption at 77 K on various samples.

Figure 1:
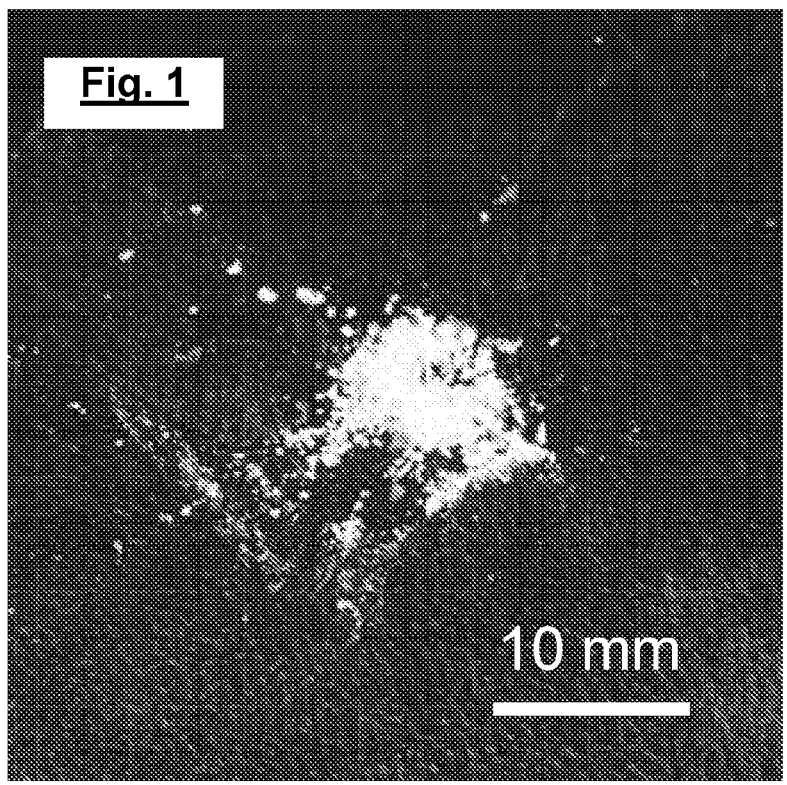

DETAILED DESCRIPTION OF THE PREFERRED EMBODIMENTS, AND FURTHER OPTIONAL FEATURES OF THE INVENTION

The embodiments of the present invention provide monolithic metal-organic frameworks (MOFs). These have utility, for example, in gas adsorption applications.

The present inventors here disclose a new way to synthesise monolithic ZIF-8 structures. This is a MOF that has received lot of attention in the last years due to its high thermal and chemical stability. The synthesis process can be a one-step process and produces robust monoliths avoiding the use of binders and/or high pressure. This therefore addresses the problems discussed above related to porosity loss and reduced mechanical properties. The work reported here concentrates on ZIF-8 as a model MOF, but the invention also applies to other MOF materials which are conventionally produced in powdery form.

Briefly stated, the monolithic ZIF-8 structure is produced at ambient temperature by mixing a solution of $Zn^{2+}$ and 2-methyl imidazole in ethanol (or another suitable solvent such as methanol or DMF), and drying at ambient conditions, optionally including a centrifugation step to speed up the removal of solvent. It can be prepared with the desired shape for industrial use in a low-cost process. Mechanical assays using nano-indentation shows that the monolithic material presents more robust mechanical properties compared with the original ZIF-8 single crystals. This is significant for industrial application in which the material may be subjected to mechanical stress. Industrial applications of the material include: gas adsorption/separation technologies, such as gas storage (e.g. $H_2$ storage), carbon capture, gas purification, such as $H_2$ and/or $CH_4$ purification, gas separation, such as ethane/ethylene separation, capture of warfare and toxic industrial compounds (e.g. xylenes, $SO_2$, ammonia, nerve agents, etc.); gas sensing; replacement of zeolites; replacement of activated carbon; coating of activated carbon; drug delivery; catalysis; and water treatment.

In contrast with crystalline ZIF-8 powder obtained from known synthesis techniques, the monoliths of the preferred embodiments of the present invention are still fully or mainly crystalline but are substantially transparent. This makes them good candidates for sensing applications.

SEM images and $N_2$ adsorption measurements show that meso- and macro-porosity is substantially absent in the preferred embodiments of the present invention. This leads to higher densities and therefore higher volumetric capacities critical for adsorption process in industrial applications.

Described below is a one-step synthetic procedure to produce crystalline monolithic ZIF-8 [$Zn(C_4H_5N_2)_2$]. These macro-scale structures are substantially more rigid than single crystals of the same composition, whereas gas adsorption studies showed that retain the characteristic porosity of ZIF-8. Monolithic structures according to preferred embodiments of the invention showed bulk densities three times higher than conventional ZIF-8.

Zeolitic imidazolate frameworks (ZIFs), a sub-family of metal-organic frameworks (MOFs), are crystalline materials prepared by self-assembly of metal ions and imidazolate organic linkers [Park et al (2006)]. ZIFs adopt zeolitic topologies and display some of the quintessential stability of these classic inorganic materials [Tian et al (2007)]. Their large pore volumes and surface areas, along with the possibility for chemical functionalization, have led to potential applications in gas adsorption, separation and catalysis [Furukawa et al (2013), Bennett et al (2013)]. However, the utility of ZIFs and MOFs in such applications is currently limited by an inability to process the microcrystalline powders resulting from their synthesis. Such shaping is very important in order to reduce the existence of pressure drops of a gas flow in columns due to powder compaction. In most cases, binders and/or high-pressure processes are used to pelletize the material, though often result in either i) partial or complete collapse of the internal porosity when using high pressures [Chapman et al (2009)], or ii) pore blocking by the binder, preventing the access to the porosity. In addition, the use of a binder per se limits the amount of MOF in the final product, and hence would be expected to lead to reduced total guest capacities.

Despite of the rapid growth of MOF research, only few reports about the development of 'monolithic' structures are available in the literature. Most of the research on circumventing these problems concentrates on the incorporation of MOFs into porous polymer monoliths [see, for example, Fu et al (2013) and Huang et al (2013)] and open-pore polymer foams [US 2010/0181212], the use of high mechanical pressure, or the use of extrusion processes [Küsgens et al (2010)]. Thus, the work reported in the literature typically does not provide monoliths of the MOF material itself, but instead monolithic supports of another material, on which the MOF is supported, or structures in which polymeric binders are required in order to hold the MOF particles together.

In the current work, we focus on ZIF-8 [Zn(mIm)$_2$] (mIm=2-methylimidazolate, $C_4H_5N_2^-$) which is a prototypical ZIF with sodalite topology. It contains large pore cavities (about 11.6 Å diameter) interconnected by small windows (about 3.4 Å diameter). Because ZIF-8 has characteristic flexibility, these windows allow guest molecules larger than themselves into the porosity through a concerted 'swinging' motion of the mIm linkers [Fairen-Jimenez et al (2011), and Fairen-Jimenez et al (2012)].

According to Fairen-Jimenez et al (2011), ZIF-8 has a specific BET surface area of 1750 m$^2$/g. According to Park et al (2006), ZIF-8 has a specific pore volume of 0.663 cm$^3$/g.

The preferred embodiments of the invention involve a low-cost method of producing robust monoliths under ambient conditions without the use of binders, high pressures or high temperatures. The monoliths produced possess higher Young's moduli than single crystals of ZIF-8 and, importantly, retain the characteristic porosity of the framework while showing higher bulk densities. Furthermore, the resultant monoliths are transparent and fluoresce (as does ZIF-8), so the work opens up a new pathway for sensing applications.

Samples were prepared from a solution of HmIm (20 ml, 0.395 M) and Zn(NO$_3$)$_2$.6H$_2$O (20 ml, 0.049 M) in ethanol, after 2 hours stirring at room temperature. After centrifugation at 5500 rpm for 10 minutes, a white solid was collected and dried by three different methods. White pellets (ZIF-8HT) were obtained from drying under vacuum at 100° C. overnight, whilst transparent monoliths (ZIF-8LT) resulted from room temperature drying overnight. A second transparent sample (ZIF-8LTHT) was obtained through further evacuation of ZIF-8LT at 100° C. overnight.

Zn(NO$_3$)$_2$.6H$_2$O (98%) and 2-methylimidazole (97%) were purchased from Alfa Aesar, ethanol (≥99.5%) were purchased from Sigma-Aldrich. All chemicals were used as received.

Solutions of HmIm (20 ml, 0.395 M) and Zn(NO$_3$)$_2$.6H$_2$O (20 ml, 0.049 M) in ethanol were mixed and stirred for 2 hours at room temperature. After centrifugation at 5500 rpm for 10 minutes, a white solid was collected and processed by four different methods. First, ZIF-8HT (HT=high temperature) was obtained by drying a fraction of the white solid at 100° C. overnight in a vacuum oven. Second, ZIF-8LT (LT=low temperature) was obtained by drying a second fraction of the white powder at room temperature overnight. Third, ZIF-8-LTHT was obtained by further evacuation of ZIF-8LT at 100° C. overnight in a vacuum oven. Finally, ZIF-8ER (ER=extended reaction) was obtained by washing the initial white solid twice in ethanol and by adding new solutions of HmIm (20 ml, 0.395 M) and Zn(NO$_3$)$_2$.6H$_2$O (20 ml, 0.049 M) in ethanol. The mixture was ultrasonicated for 10 minutes at room temperature, centrifuged at 5500 rpm and dried at room temperature overnight.

Figure 2:
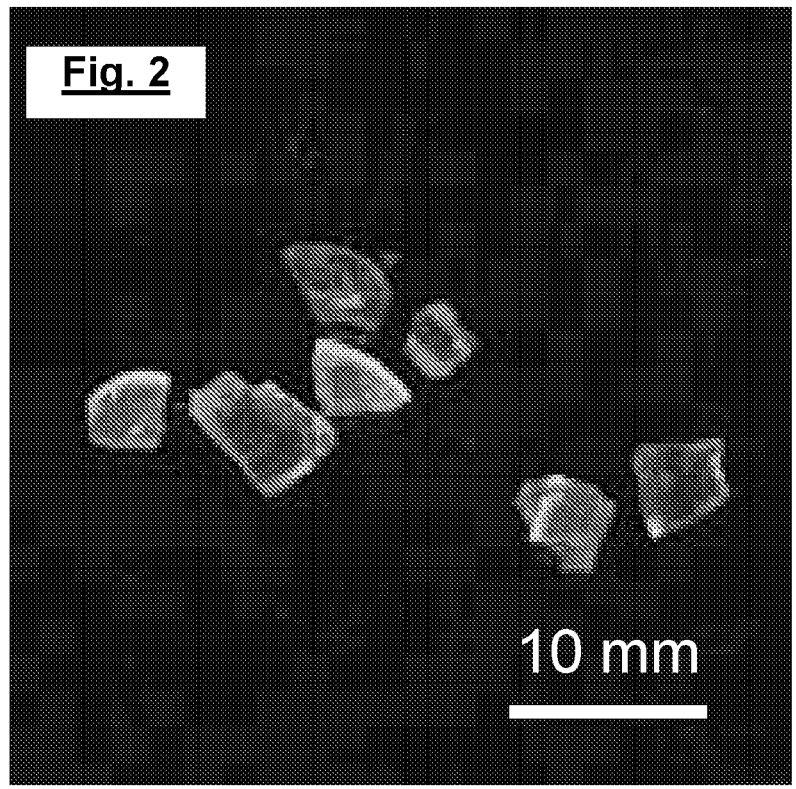

FIGS. 1-4 show optical micrographs at relatively low magnification. FIG. 1 shows ZIF-8HT. FIG. 2 shows ZIF-8LT. It is possible to produce similar monoliths of ZIF-8LTHT. FIG. 3 shows ZIF-8ER under normal illumination and FIG. 4 shows ZIF-8ER under 365 nm UV light.

Figure 5:
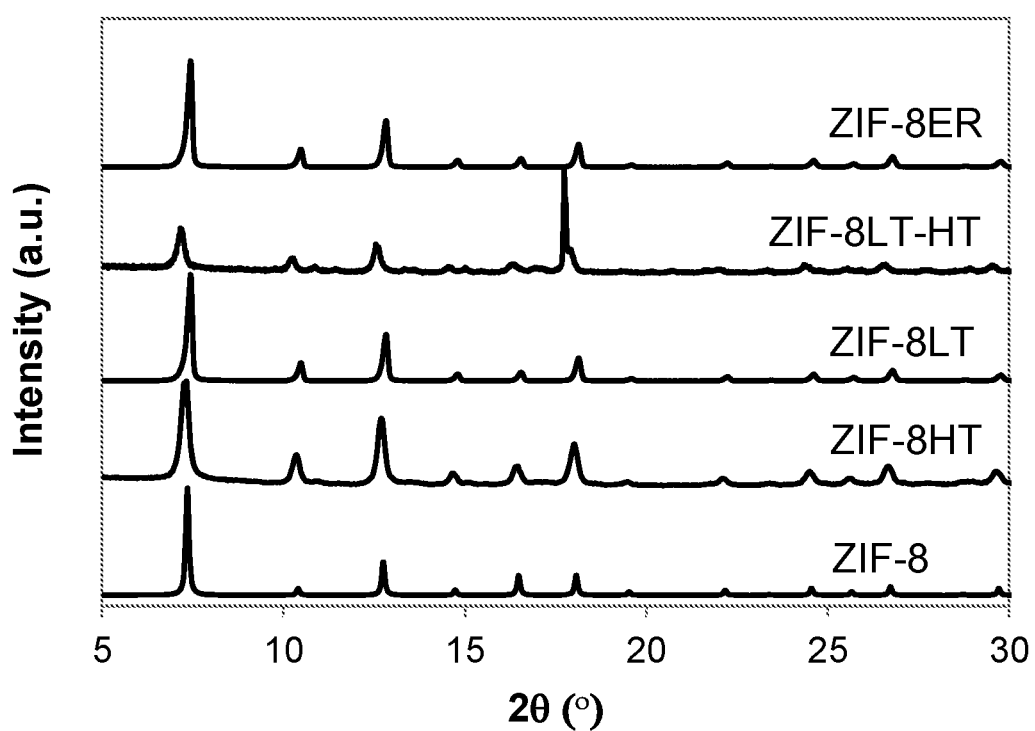
FIG. 5 shows powder X-ray diffraction (PXRD) patterns of the different samples alongside a simulated pattern for ZIF-8.

FIG. 5 shows powder X-ray diffraction (PXRD) patterns of the different samples alongside a simulated pattern for ZIF-8.

As shown in FIG. 1, the white pellets of ZIF-8HT easily disaggregated into a typical white ZIF-8 powder. However, both ZIF-8LT (see FIG. 2) and ZIF-8LTHT remained as substantially transparent monolithic structures. The fact that ZIF-8LT retained its macroscopic monolithic morphology during higher temperature activation (i.e. during the treatment to form ZIF-8LTHT) is remarkable.

FIG. 4 shows the fluorescence of ZIF-8ER, which sample is discussed in more detail below. The substantially transparent nature of the preferred embodiments makes the material a perfect candidate for sensing applications.

Figure 6:
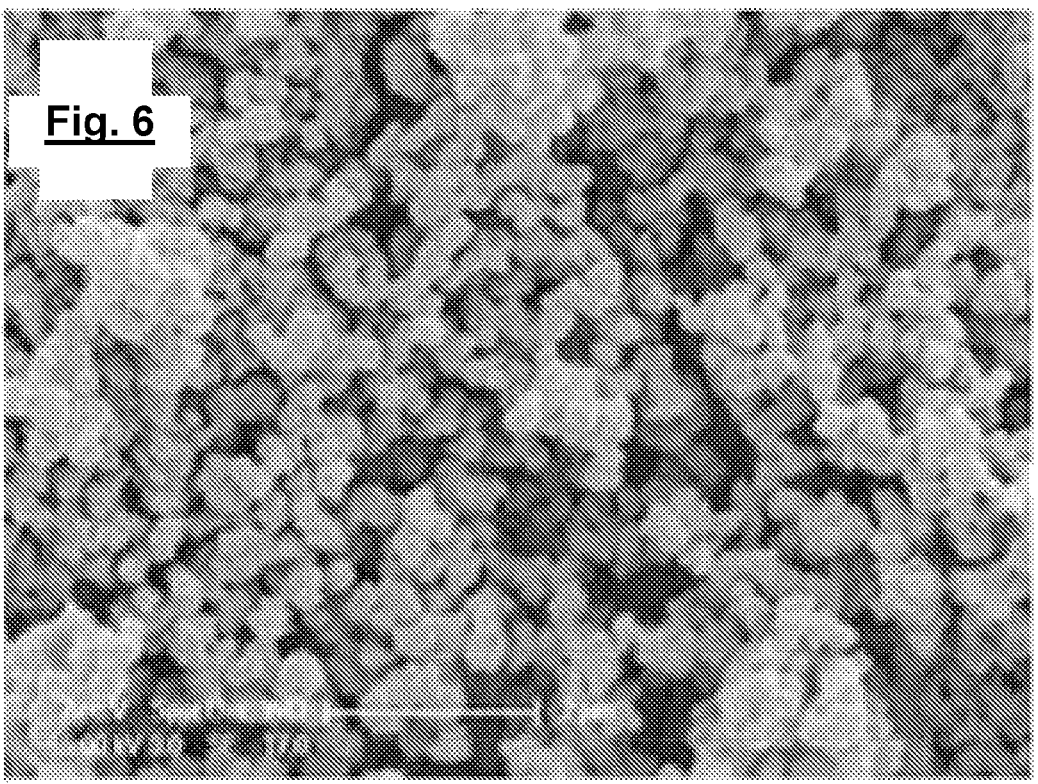
FIGS. 6, 7 and 8 show SEM micrographs of ZIF-8-HT, ZIF-8-LT and ZIF-8-ER, respectively.
Figure 7:
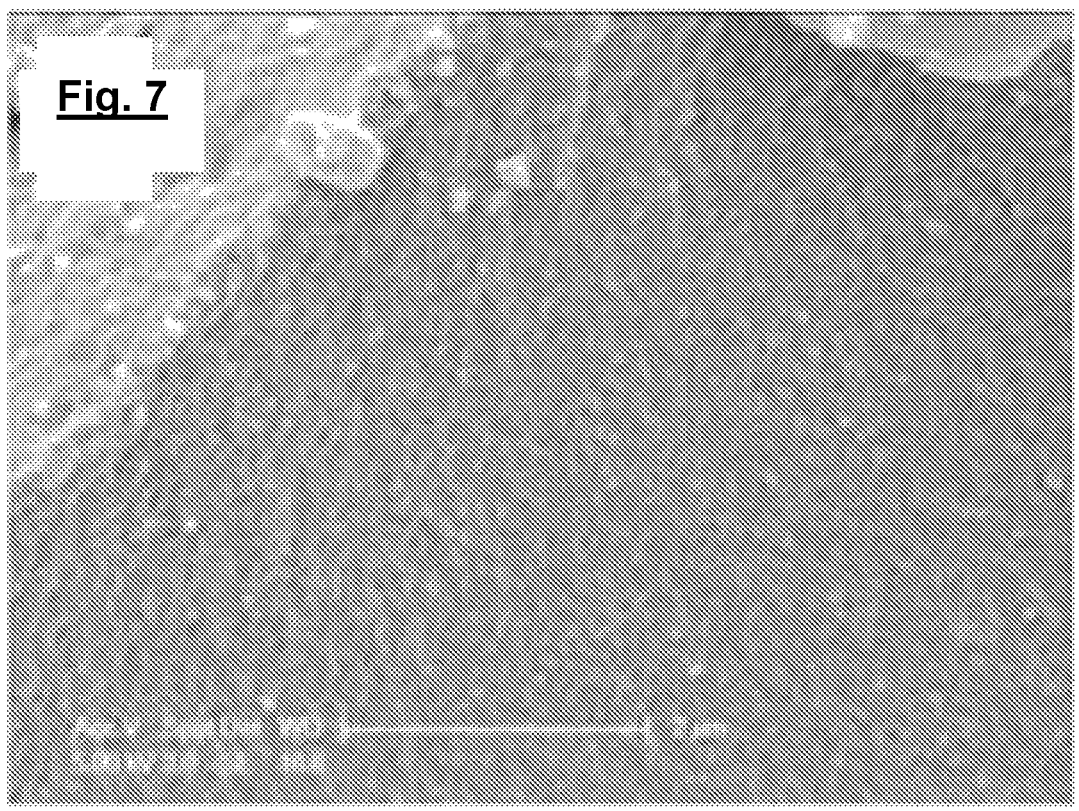
Figure 8:

FIG. 5 shows the powder X-ray diffraction (PXRD) pattern of the different samples. The three samples are identical in crystalline structure, despite the differences in their morphologies. The present inventors investigated these differences using scanning electron microscopy (SEM). FIGS. 6, 7 and 8 show SEM micrographs of ZIF-8HT, ZIF-8LT and ZIF-8ER, respectively. FIGS. 6, 7 and 8 show that ZIF-8HT presents a significant volume of interstitial spaces between primary particles, associated to pores in the range of the meso- and macroporosity, whereas ZIF-8LT and ZIF-8ER present relatively flat surfaces. The different morphologies at the macro- and micro-scale resemble those previously observed for xerogels and aerogels [Lohe et al (2009), Li et al (2013)], not only for amorphous MOF-like materials [Lohe et at (2009)] but also for carbon and silica aerogels [Fairen-Jimenez et at (2008), Fairen-Jimenez et at *Carbon* (2006)]. Primary particle sizes of ZIF-8 from the initial mixture of precursors, obtained by transmission electron microscopy (TEM), were around 60-70 nm.

Table 1 below shows the mechanical properties of elastic modulus (Young's modulus) and hardness for different ZIF-8 structures.

TABLE 1

| Material | Elastic Modulus GPa | Hardness GPa |
|---|---|---|
| ZIF-8 single crystal [Tan et al (2010)] | 2.973 ± 0.051 | 0.501 ± 0.023 |
| ZIF-8-LT | 3.66 ± 0.18 | 0.417 ± 0.038 |
| ZIF-8-LTHT | 3.57 ± 0.22 | 0.429 ± 0.026 |
| ZIF-8-ER | 7.04 ± 0.13 | 0.643 ± 0.021 |

The data for the single crystal was obtained in the {1, 0, 0} facet.

The microcrystalline nature of ZIF-8HT precluded investigation of the Young's modulus, E, and hardness, H, by nano-indentation, though monoliths of ZIF-8LTHT were of sufficient size to allow characterisation.

Table 1 shows comparable H values to those seen before, though Young's moduli were significantly higher. In some cases, measurements could only be performed on one face of the monoliths because of the small area available on others.

In order to use MOF-monoliths in e.g. column beds or fuel tanks, they must have appropriate mechanical properties to support mechanical stresses, which come from the weight of the adsorbent inside the columns and from vibrations or movements of the bed.

Without wishing to be bound by theory, the present inventors consider that the formation of the monolithic structures stems from the existence of small primary particles and the mild drying conditions. The fact that ZIF-8LT and ZIF-8LTHT are transparent and therefore do not show light scattering is presumably related to the absence of electronic contrast between phases [Fairen-Jimenez et al J. Phys. Chem. (2006),] or the existence of primary particles smaller than the light wavelength [Apetz and van Bruggen (2003)]. At the time of writing, the present inventors hypothesise that the existence of residuary reactants (Zn ions and mlm) within the sample and the mild drying process allows extension of the polymerisation reaction and the formation of the monolithic structure. In this case, new ZIF-8 is formed during the drying process of ZIF-8LT at room temperature, acting as a binder of the primary ZIF-8 particles.

To investigate this hypothesis, the present inventors proceeded with the synthesis of a new sample where the initial precipitate, immediately after centrifugation, was included in a new solution of mlm and $Zn(NO_3)_2.6H_2O$ in ethanol. This mixture was ultrasonicated for 10 minutes at room temperature, centrifuged at 5500 rpm and dried at room temperature overnight. The resulting white but partially transparent monolithic structure was named the extended-reaction sample, ZIF-8ER. As can be seen in Table 1, ZIF-8ER is significantly more rigid than the previous monoliths and the ZIF-8 single crystal. The high values of E reported can be compared to thin films (i.e. not monoliths) of ZIF-8 (3.5 GPa) prepared by Eslava et al (2012), where the deviation in moduli from single crystals was assigned to surface roughness effects.

Notable differences in E between thin films of HKUST-1 [Bunschuh et al (2012)] (9.3 GPa and 3.5 GPa) of HKUST-1 have been noted before and ascribed to elastic anisotropic effects.

The porosity of the prepared samples was analysed using $N_2$ adsorption at 77 K. FIGS. 9A and 9B show the results in a semi-logarithmic and linear scale, respectively. The data points in FIGS. 9A and 9B are: ZIF-8-LT—squares; ZIF-8-HT—triangles; and ZIF-8-LTHT—diamonds. Note the use of semi-logarithmic scale allows more detail to be seen for the low pressure range. Table 2 reports the main results. For comparison with FIGS. 9A and 9B. the theoretical single crystal capacity would be represented by a horizontal line at about 420 $cm^3$/g STP.

The effect of the density differences between samples on the volumetric adsorption is very significant. First, the low density of powder ZIF-8 means that the volumetric capacity, BET volumetric area and micropore volume are very low. Then, the monolithic materials prepared here present an outstanding enhancement of the conventional, powder ZIF-8, with values more than 3 times higher: 1660 vs. 485 $m^2$ $cm^{-3}$ for ZIF-8ER and powder ZIF-8, respectively, due to the high densities. The fact that the volumetric adsorption capacity is higher than the theoretical single crystal capacity, which is calculated from the 18 mmol $g^{-1}$ $N_2$ capacity and a crystal density of 0.95 g $cm^{-3}$ could be related to the existence of issues when calculating bulk densities or the existence of impurities. Efforts towards MOF densification have been addressed before for MOF-177 [Zacharia (2010)], where the density of MOF-177 increased from 0.1 g $cm^{-3}$ up to 1.40 g $cm^{-3}$. However, in all the cases the volumetric capacities were below the theoretical single crystal capacities. The fact that the maximum volumetric capacity for MOF-177 was obtained for pellets with a density of 0.53 g $cm^{-3}$ before decreasing for higher preparation pressures suggest a gradual amorphization when using higher pressures, causing the collapse of the porosity. This was indeed confirmed by XRD studies on the pellets obtained at very high pressures.

All the samples presented the typical step-wise adsorption mechanism of $N_2$ in ZIF-8, which indicate the samples were indeed microporous. In addition, ZIF-8-HT showed higher adsorption at higher pressures, close to saturation pressure, which is consistent with the existence of meso- and macroporosity observed in the SEM. The gravimetric BET areas were around 1390 $m^2$/g, whereas gravimetric BET areas of ZIF-8 are generally in the range of 1300-1600 $m^2$/g [Song et al (2012)], meaning that the monolithic materials retained the characteristic porosity of ZIF-8. Moreover, volumetric adsorption capacities (i.e. the amount of gas that can be adsorbed per $cm^3$ of a specific material) and volumetric BET areas, which can be obtained by multiplying gravimetric data with bulk density of the sample, are especially important from an applied point of view in most industrial applications when the adsorbent material has to be confined in a fixed given volume.

These differences were studied by measuring the density of the samples using mercury porosimetry. Since mercury does not penetrate the porosity of the materials at atmospheric pressure, it allows the measurement of the bulk density of the samples by applying Archimedes' method, which in turn facilitates calculation of their bulk densities.

Table 2, below, shows data for BET area ($S_{BET}$), micropore volume ($W_0$), meso-pore volume ($V_2$) (note that $N_2$ adsorption analysis typically probes porosity only up to 50 nm), total pore volume ($V_{Tot}$) and bulk density ($\rho_b$) for the different ZIF-8 structures.

TABLE 2

| Material | $S_{BET}$ $m^2$/g | $W_0^a$ $cm^3$/g | $V_2$ $cm^3$/g | $V_{Tot}^b$ $cm^3$/g | $\rho_b^c$ g/$cm^3$ | $S_{BET}$(vol) $m^2$/$cm^3$ | $W_0$(vol) $cm^3$/$cm^3$ | $V_2$(vol) $cm^3$/$cm^3$ | $V_{Tot}$(vol) $cm^3$/$cm^3$ |
|---|---|---|---|---|---|---|---|---|---|
| ZIF-8HT | 1387 | 0.552 | 0.277 | 0.829 | $0.35^d$ | 485 | 0.193 | 0.097 | 0.29 |
| ZIF-8LT | 1359 | 0.532 | 0.011 | 0.543 | 1.14 | 1549 | 0.606 | 0.013 | 0.619 |
| ZIF-8LTHT | 1423 | 0.543 | 0.003 | 0.546 | 1.05 | 1494 | 0.570 | 0.003 | 0.573 |

TABLE 2-continued

| Material | $S_{BET}$ m²/g | $W_0{}^a$ cm³/g | $V_2$ cm³/g | $V_{Tot}{}^b$ cm³/g | $\rho_b{}^c$ g/cm³ | $S_{BET}(vol)$ m²/cm³ | $W_0(vol)$ cm³/cm³ | $V_2(vol)$ cm³/cm³ | $V_{Tot}(vol)$ cm³/cm³ |
|---|---|---|---|---|---|---|---|---|---|
| ZIF-8ER | 1395 | 0.535 | 0.010 | 0.545 | 1.19 | 1660 | 0.637 | 0.012 | 0.648 |
| ZIF-8 single crystal [e] | 1706 | 0.74 | — | 0.74 | 0.95 | 1620 | 0.70 | — | 0.70 |

[a] Obtained at $P/P_0 = 0.1$
[b] Obtained at $P/P_0 = 0.98$
[c] Bulk density quantified by measurement of weight and volume using mercury porosimetry
[d] ZIF-8 tap bulk density as reported by BASF
[e] Reference Fairen-Jimenez et al [2011]

The single crystal density of ZIF-8 is high (about 0.95 cm³/g). However, of course in a particulate format, the inter-particle space takes up a substantial portion of the bulk volume of a powder material. In the case of ZIF-8, it is expected that the inter-particle space results in the powder having a tap bulk density of about 50% of the single crystal density [Juan-Juan et al (2010)]. Indeed, commercial ZIF-8 from BASF (Basolite® Z1200) presents a bulk density of 0.35 g/cm³ [see URL: http://www.sigmaaldrich.com/catalog/product/aldrich/691348?lang=en&region=GB accessed 10 Jun. 2014]. In contrast, all the monolithic structures of the preferred embodiments revealed very high bulk densities, which is especially important from an applied point of view when the adsorbent material has to be confined in a given volume. The fact that measured densities are higher than crystal density of ZIF-8 suggests the presence of denser, amorphous phases or a non-complete activation, and therefore slightly lower gravimetric surface areas. When translating the BET areas and micropore volumes into volumetric, the monolithic materials present more than 3 times higher values than conventional, powder ZIF-8.

Figure 39:
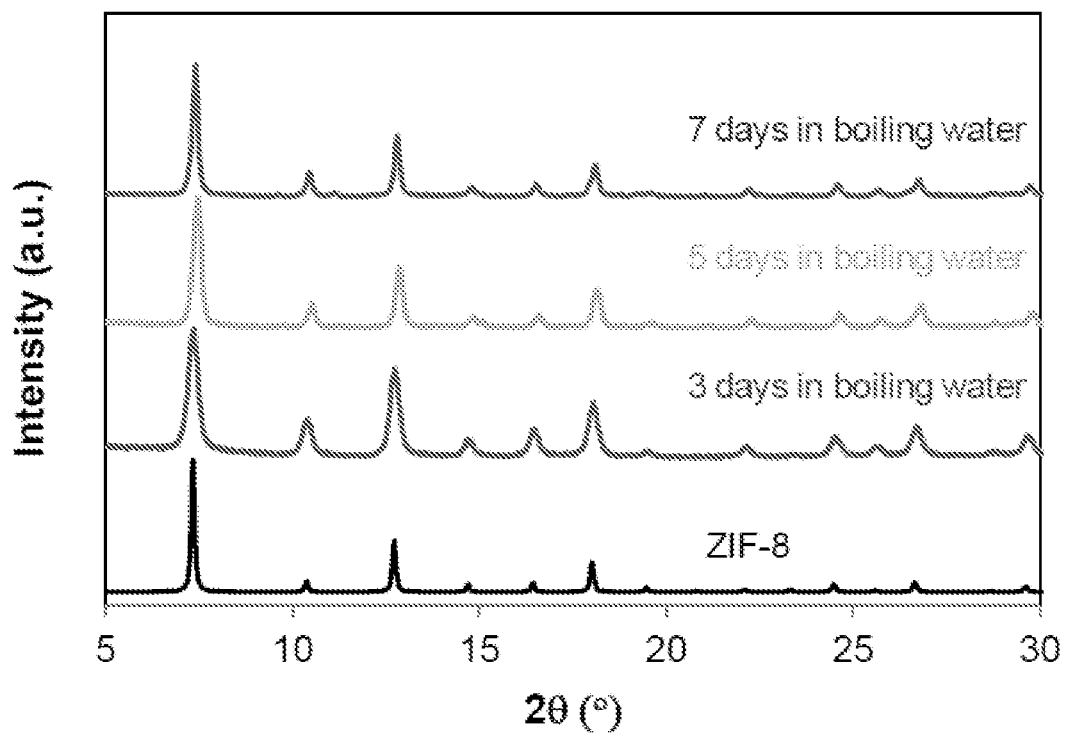
FIG. 39 shows the PXRD patterns of monolithic of ZIF-8ER after immersion in water at 100° C. for 3, 5 and 7 days.

The stability of the monolithic ZIF-8ER was tested in water at 100° C. for 7 days. FIG. 39 shows the PXRD patterns of the samples at 3, 5 and 7 days. After being immersed in boiling water, ZIF-8ER was able to keep the monolithic morphology and the crystalline structure of ZIF-8, similar to previous reported data for standard, powder ZIF-8.

In the examples reported above, the samples were manufactured without the deliberate addition of components other than solvent and the components needed to form the MOF. In other embodiments, it is possible to include other components. Such other components may be included, for example, to increase the meso- or macro-porosity of the monoliths, where that is wanted for a particular application. In this case, it is typical that the composition of the monolith cannot be considered to be equivalent to the composition of a MOF single crystal. Instead, the composition of the monolith can be considered to be equivalent to the composition of a MOF single crystal and one or more remaining components of the composition (i.e. the additives). In order to make a fair assessment of the properties of the monolith for a particular property (e.g. BET surface area, porosity, pore size distribution, Young's modulus, hardness, etc.), the property of the monolith is compared with a volumetric weighted arithmetic mean of the corresponding property of the MOF single crystal and said remaining components. Thus, for example, when the composition of the monolith can be considered to be 80% by volume of a MOF material capable of forming a MOF single crystal having Young's modulus $E_0$ and 15% by volume of a first additive having Young's modulus $E_1$ and 5% by volume of a second additive having Young's modulus $E_2$, then the volumetric weighted arithmetic mean of the Young's modulus of the MOF single crystal and the remaining components is: $[0.8E_0+0.15E_1+0.05E_2]$.

Figure 10:
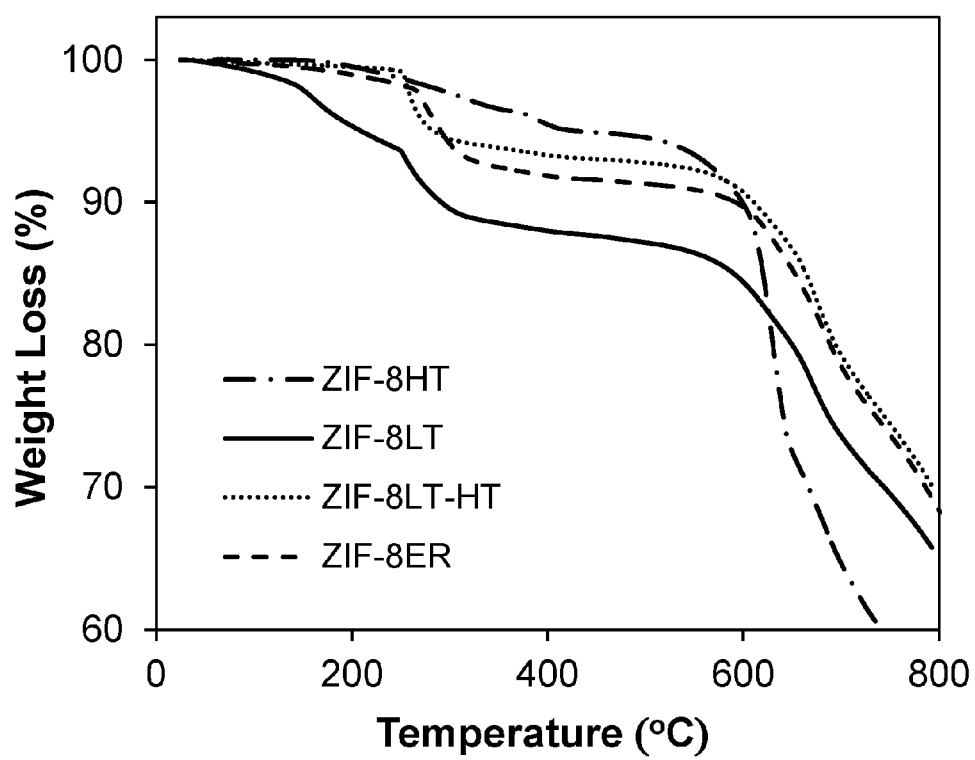
FIG. 10 shows the results of thermogravimetric analysis (TGA) on various samples.

FIG. 10 shows the results of thermogravimetric analysis (TGA) of the different samples. This provides information on the stability of the samples. FIG. 10 shows weight losses of 12, 7 and 8% between 150-300° C. for ZIF-8LT, ZIF-8LTHT and ZIF-8ER respectively. These losses are attributed to the residual ethanol and water in the materials. ZIF-8-HT shows about 4% weight loss between 150-300° C., indicating that the residual solvent molecules in monoliths are more difficult to be removed than in powders. A second weight loss step due to thermal degradation is observed at 600° C. for all three samples, which is consistent with the previous literature reports [e.g. Park et al (2006)].

In summary, disclosed above is the synthesis of transparent monoliths of ZIF-8 by a one step process using mild conditions. Monolithic materials retained the characteristic porosity of ZIF-8 while showing bulk densities three times higher than conventional ZIF-8. In addition, samples were substantially more rigid than single crystals of the same composition. All these characteristics make the reported process ideal for industrial applications where optimal materials need to present high volumetric adsorption capacities and satisfactory mechanical properties.

MOF Layers/Coatings

The same synthesis principle as for the monolithic MOFs reported above has been used to create MOF layers (also called coatings here) coatings on substrates. The synthesis method of the ZIF-8 coating, named here ZIF-8N, was similar to that of ZIF-8LT reported above. After 2 hours reaction under stirring, the white solution was allowed to settle for 30 minutes. After most of the white solids precipitate, 30 ml of the supernatant were carefully removed using a pipette. The rest of the solvent as well as the solids were poured into a petri dish and dried for 24 hours at ambient conditions. The resultant ZIF-8 coating formed on the base of the petri dish (the substrate) was firmly attached to the petri dish (it was difficult to remove it) and was substantially transparent. A suitable determination of substantial transparency applicable to layers of embodiments of the present invention can be made as based on the approach set out with respect to the fifth or sixth aspect of the invention.

Examples Based on Other MOF Compositions

The work reported above relates primarily to ZIF-8. However, the present invention is no necessarily limited to ZIF-8. Further embodiments of the invention use different MOF compositions. The present example relates to the MOF material ZIF-zni.

Switching the organic linker from 2-methylimidazole (the one used in ZIF-8) to imidazole allows the preparation of ZIF-zni. In the synthesis method here, a ZIF-zni monolith was obtained using a similar method to that of ZIF-8 MOF.

1 ml of NaOH (1 M) (in order to improve the deprotonation of the organic linker) was added to a solution of imidazole (20 ml, 0.395 M) in ethanol. It was then mixed with a solution of $Zn(NO_3)_2 \cdot 6H_2O$ (20 ml, 0.049 M) in ethanol, and stirred for 1 hour at room temperature. After centrifugation of the solution at 5500 rpm for 10 minutes, a white solid was collected and dried at room temperature overnight to form a monolith. In this case, a substantially identical monolithic material was observed as for ZIF-8ER.

Figure 29:
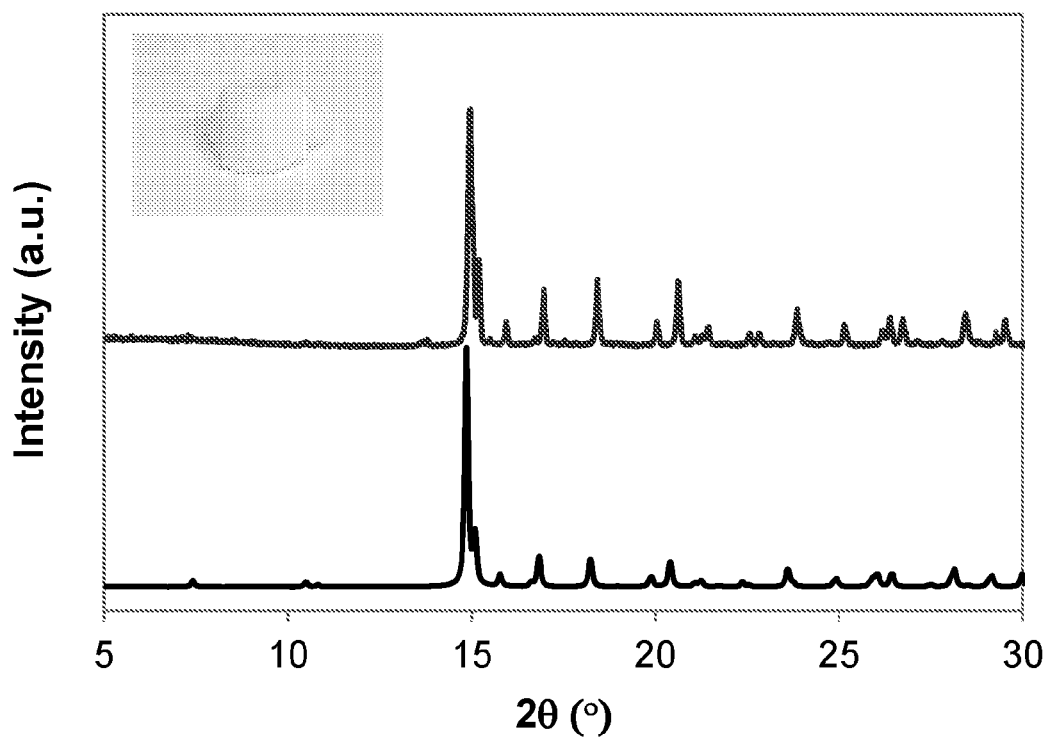
FIG. 29 shows the PXRD pattern of a ZIF-zni monolith, alongside a simulated pattern for ZIF-zni. The inset shows a view of the monolith, in a similar manner to FIGS. 2 and 3.

FIG. 29 shows the PXRD pattern of the monolith (upper PXRD trace), confirming that the structure was ZIF-zni by comparison with a known ZIF-zni PXRD trace (lower PXRD trace), The inset shows a view of the monolith, in a similar manner to FIGS. 2 and 3.

MOF@ZIF-8 Composite Monoliths

In order to combine the properties of MOFs with, for example, different selectivity, different hydrophilicity/hydrophobicity, etc., a series of hydrophilic MOFs were prepared. These were UiO-66, MIL-101 and ZIF-90. These were subsequently embedded in a matrix of hydrophobic ZIF-8, in different MOF:ZIF-8 proportions, where ZIF-8 is working as a binder. In this way, composite MOF monoliths were formed. This approach can be considered to be a generalisation from the special case of the extended reaction samples discussed above.

UiO-66 was synthesised by using the method reported by Katz et al. (2013). 0.75 g of zirconium chloride were dissolved in 30 ml DMF with 6 ml HCl (37%). A solution of 0.738 g of terephthalic acid in 60 ml DMF was then added. The mixture was heated at 80° C. overnight. The obtained solid was washed with hot DMF (70° C., 100 ml, 3 times) and ethanol (20 ml, 3 times) respectively, and dried at 80° C. under vacuum.

MIL-101 was synthesised following the procedures from Khan et al. (2011). 0.532 g of $CrCl_3 \cdot 6H_2O$, 0.332 g of terephthalic acid and 20 ml of deionized water were mixed in a 45 ml autoclave. The mixture was ultrasonicated for 20 minutes before being heated at 210° C. for 24 hours. The obtained solid was washed in hot DMF (70° C., 100 ml, 3 times) and ethanol (20 ml, 3 times) respectively, and dried at 80° C. under vacuum.

ZIF-90 was synthesised following the method reported by Shieh et al. (2013). 0.48 g of imidazole-2-carboxaldehyde (ICA) and 0.5 g of polyvinylpyrrolidone (PVP, MW: 40000) were dissolved in 12.5 ml of deionized water. A solution of 0.371 g of $Zn(NO_3)_2 \cdot 6H_2O$ in 12.5 ml of ethanol was then added. The mixture was stirred at room temperature for 3 minutes. The solid obtained after centrifugation was washed 3 times with ethanol and dried at 80° C. under vacuum.

In a typical reaction to form a MOF composite, 0.04 g of UiO-66, MIL-101 or 0.02 g of ZIF-90 were dispersed in 40 ml of ethanol, respectively, and ultrasonicated for 20 minutes. For each MOF solution, 0.649 g of 2-methylimidazole was added and ultrasonicated for 3 additional minutes until it was all dissolved. Then, 0.293 g of $Zn(NO_3)_2 \cdot 6H_2O$ were added. The mixtures were ultrasonicated for 10 minutes and the obtained solids were washed in ethanol (20 ml, 3 times) under ultrasonication for 3 minutes and dried at room temperature overnight. The derived samples were labelled as UiO-66@ZIF-8 monolith, MIL-101@ZIF-8 monolith and ZIF-90@ZIF-8 monolith respectively.

Figure 30:
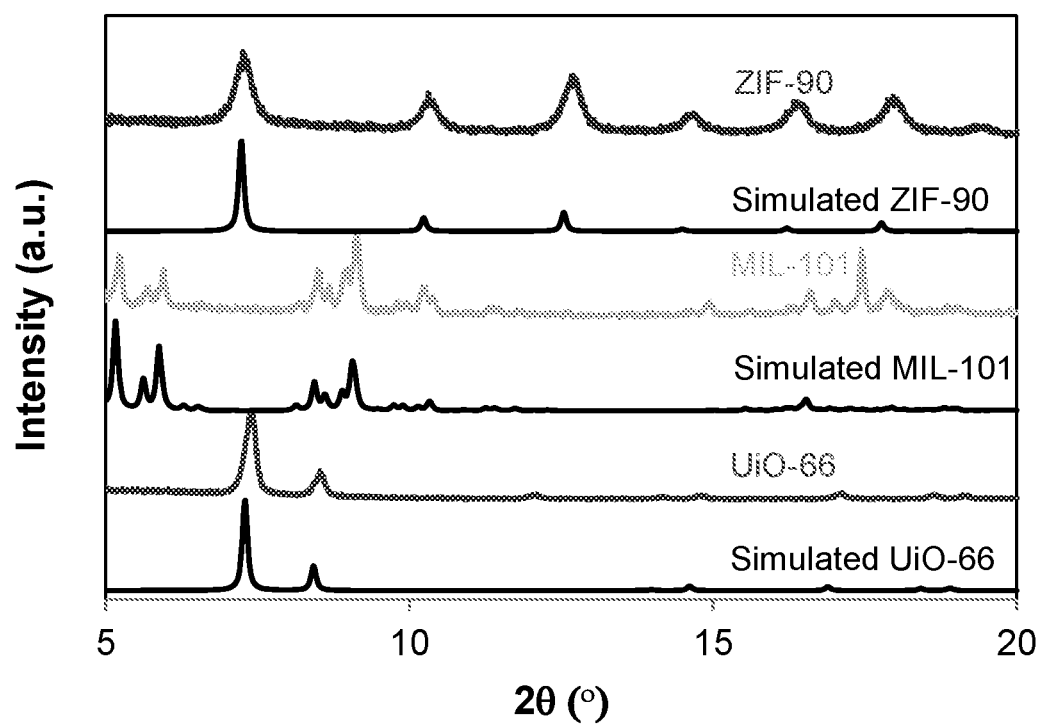
FIG. 30 shows PXRD patterns of UiO-66, MIL-101 and ZIF-90, synthesized in the present work along with their simulated patterns.

FIG. 30 shows the PXRD pattern of UiO-66, MIL-101, and ZIF-90 compared with simulated patterns. The agreement indicates the success in the synthesis of the MOFs.

Figure 31:
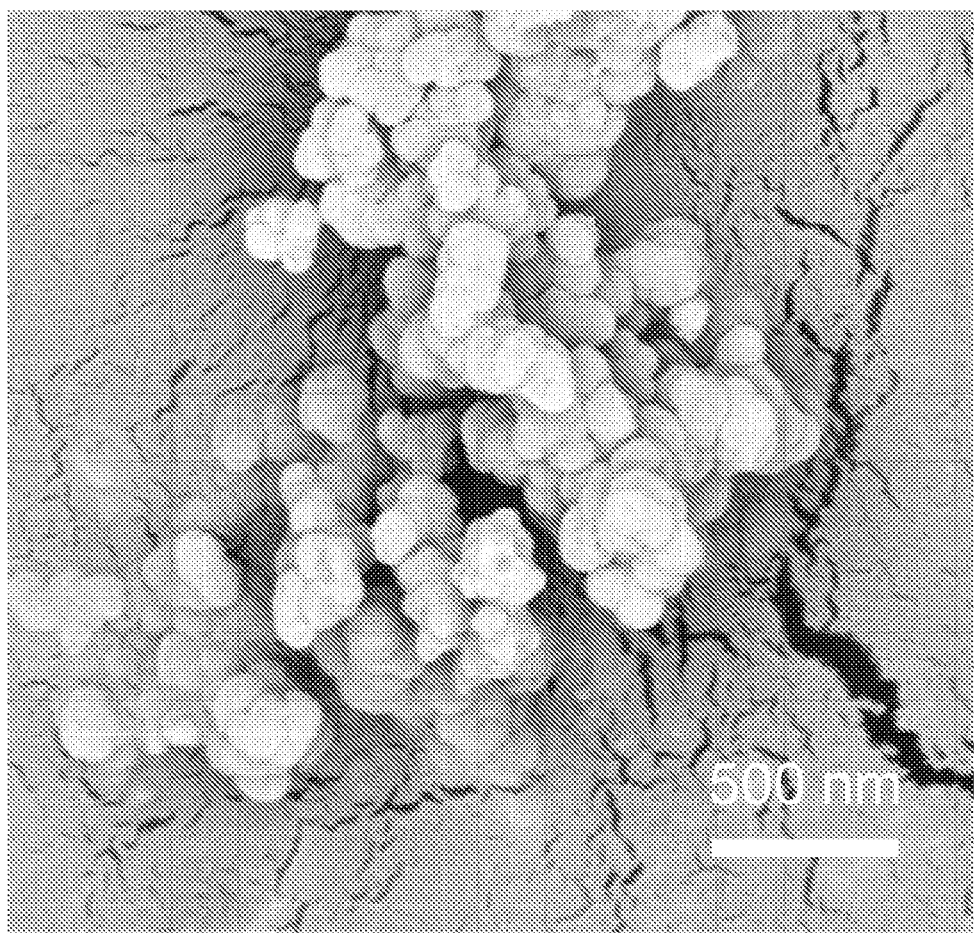
FIGS. 31-33 show SEM images of UiO-66, MIL-101 and ZIF-90 synthesized in the present work, respectively.
Figure 32:
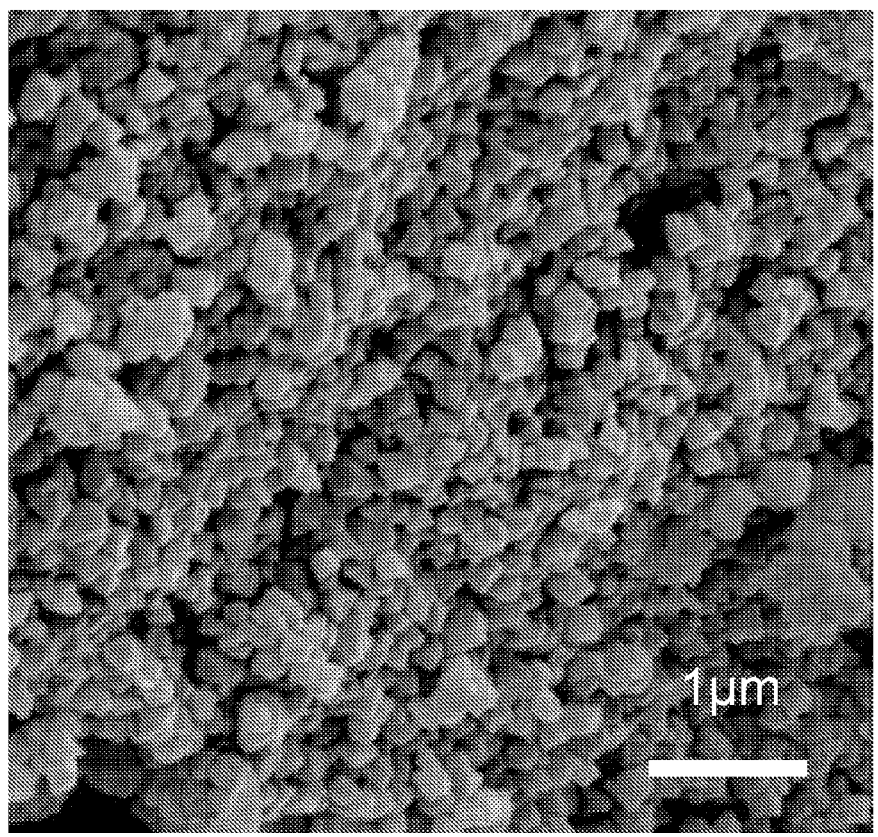
Figure 33:
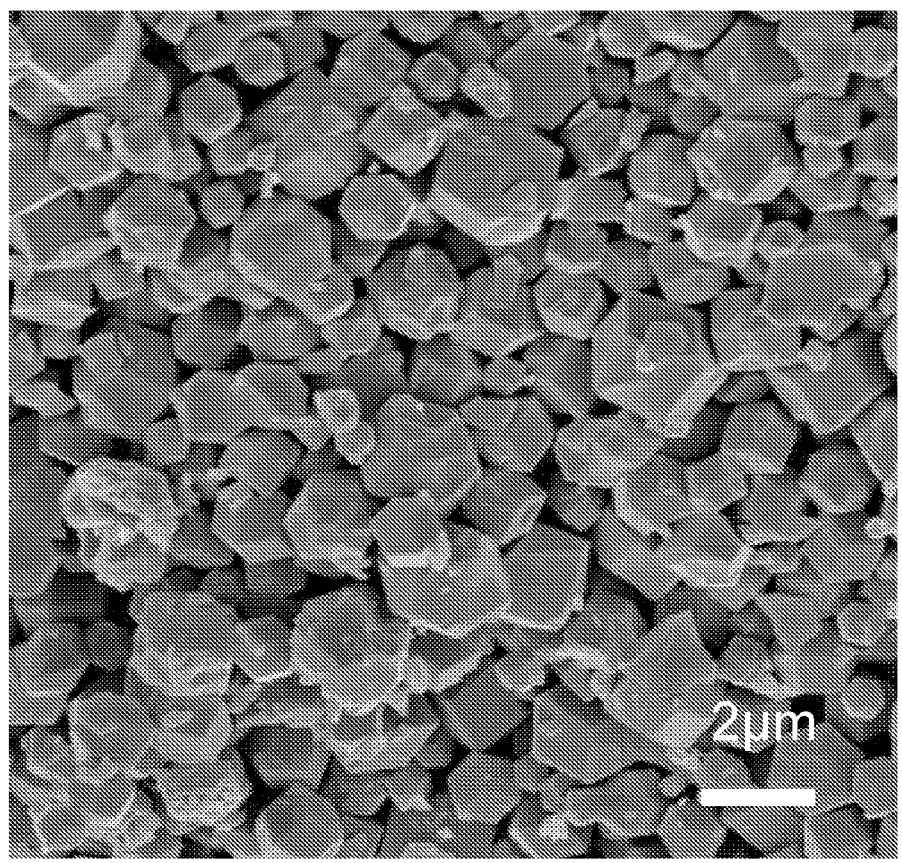

FIGS. 31-33 show the SEM images of the synthesised UiO-66, MIL-101 and ZIF-90, respectively. UiO-66 has a particle size of 100-150 nm; MIL-101 has a size of 400-500 nm; and ZIF-90 has a size around 2 μm. The MOFs are synthesised as small particles to inhibit the precipitation during the synthesis of MOF@ZIF-8 monoliths.

Figure 34:
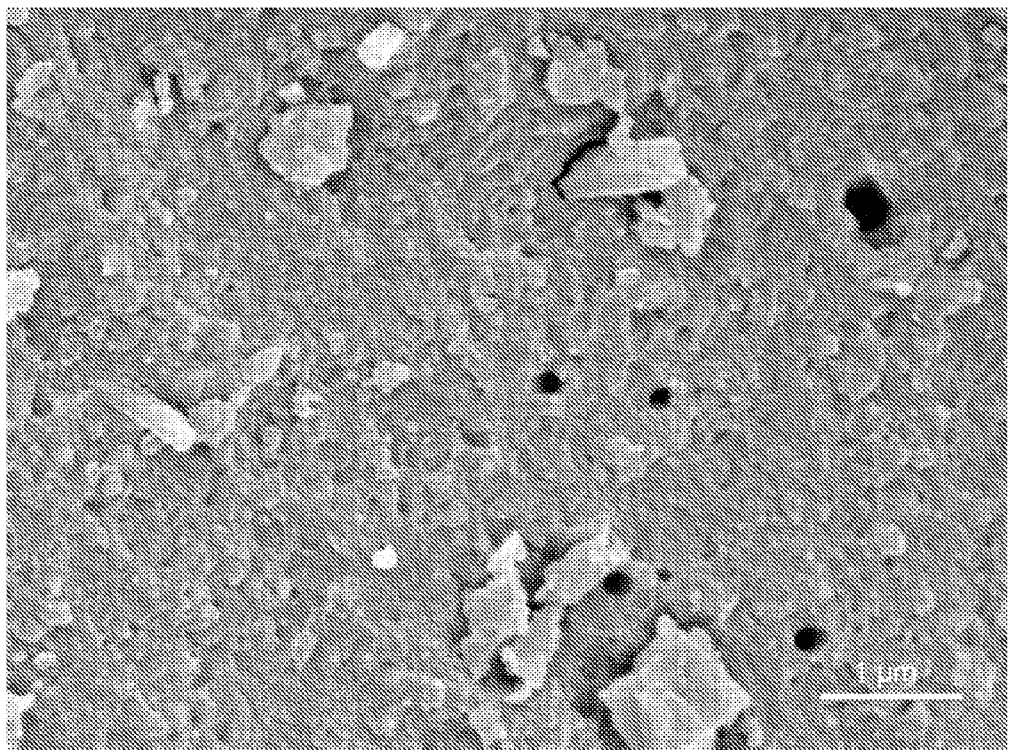
FIGS. 34 and 35 show SEM images of the cross-section of the MIL-101@ZIF-8 and ZIF-90@ZIF-8 composite monoliths, respectively.
Figure 35:
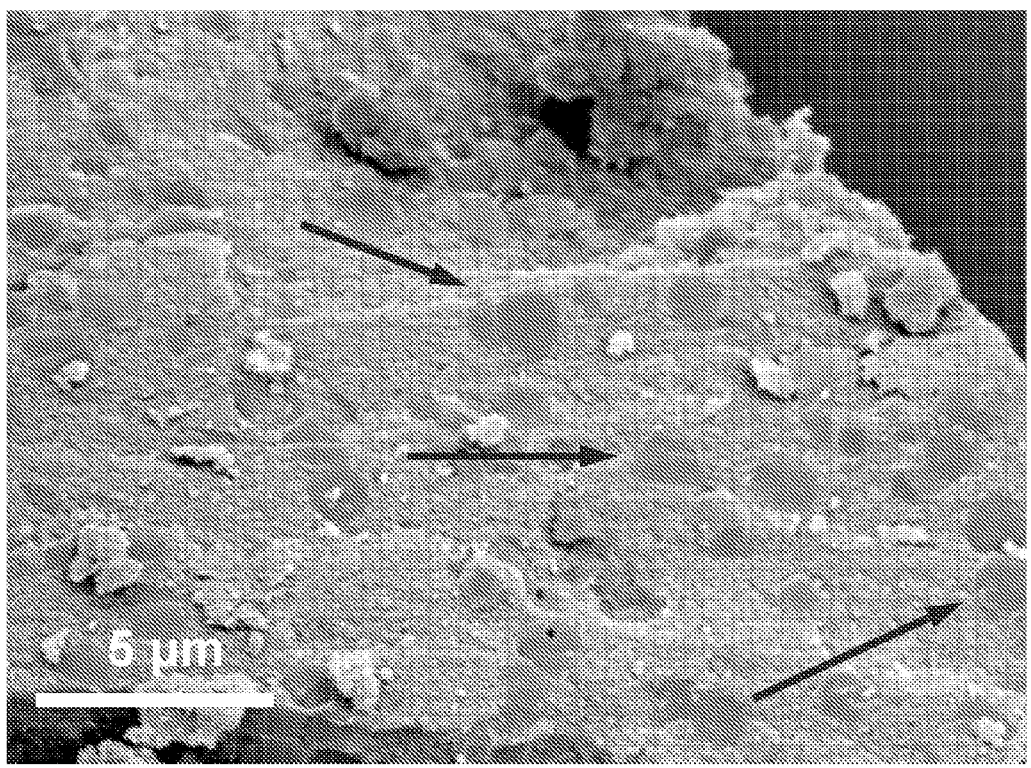

FIGS. 34 and 35 show SEM images of the cross-section of the interior of a MIL-101@ZIF-8 and a ZIF-90@ZIF-8 monolith composite, respectively. In the case of MIL-101@ZIF-8 there are some holes on the cross-section as well as some large particles isolated on the flat surface. The diameter of the holes and particles are around 400-500 nm, similar to the size of the synthesised MIL-101 particles. In the case of ZIF-90@ZIF-8 the effect is even clearer, with particles of size about 2 μm—similar to the size of the synthesised ZIF-90 particles—embedded in a matrix.

Figure 36:
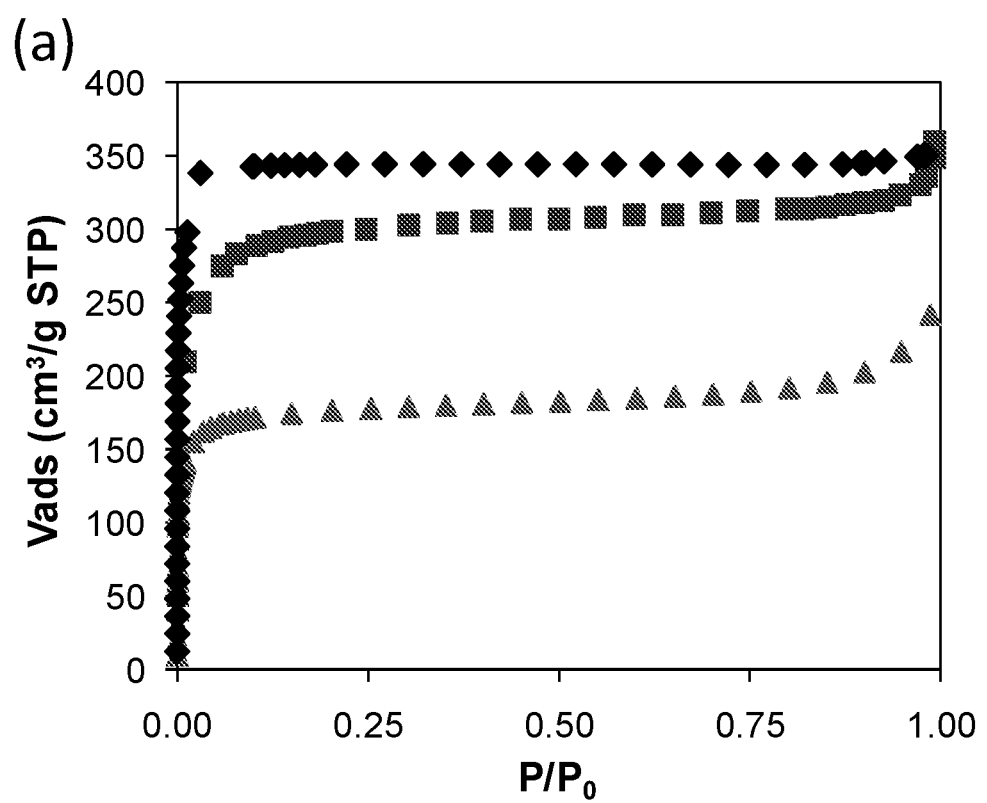
FIG. 36 shows $N_2$ isotherms of ZIF-8LT (diamonds), UiO-66 (squares) and UiO-66@ZIF-8 (triangles)
Figure 37:
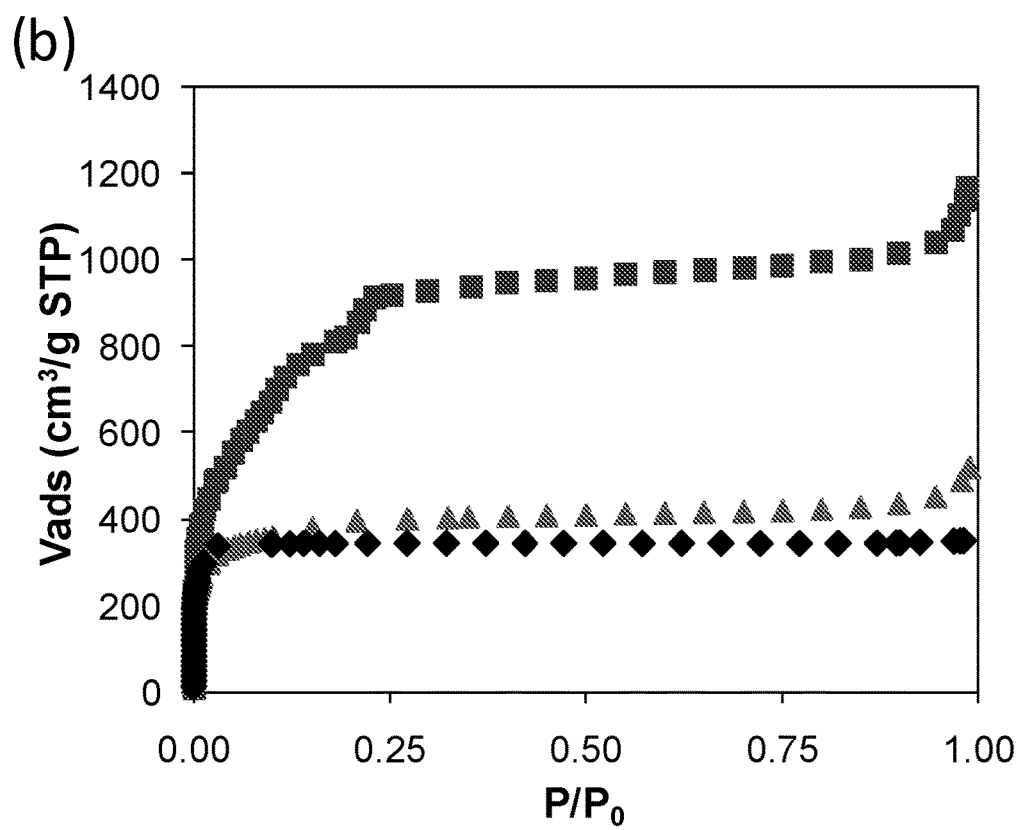
FIG. 37 shows $N_2$ isotherms of ZIF-8LT (diamonds), MIL-101 (squares) and MIL-101@ZIF-8 (triangles).
Figure 38:
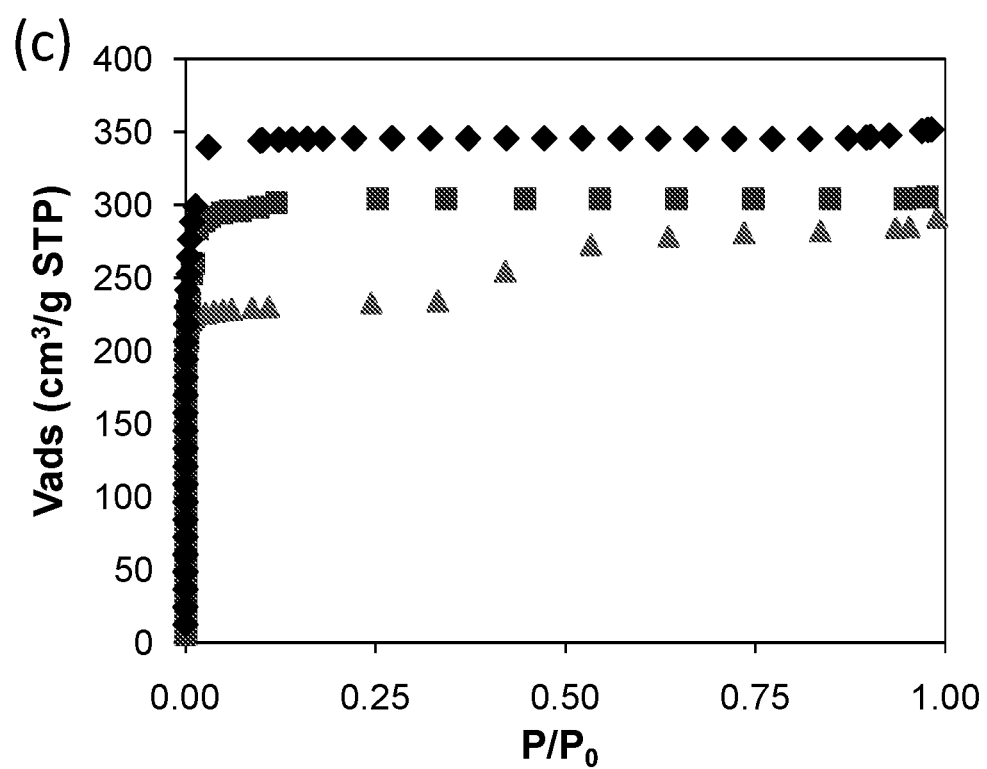
FIG. 38 shows $N_2$ isotherms of ZIF-8LT (diamonds), ZIF-90 (squares) and ZIF-90@ZIF-8 (triangles).

FIGS. 36-38 Table 3 show the $N_2$ adsorption isotherms and BET areas for different composites, respectively. As showed by the $N_2$ isotherms, the porosity properties of the composites are a combination of ZIF-8 and the included MOF. However, the BET areas of the composites are reduced compared with the theoretical value. For UiO-66@ZIF-8 and MIL-101@ZIF-8 composites, the experimental BET areas are around 500 $m^2/g$ lower than the theoretical values. In the case of the ZIF-90@ZIF-8 composite, the BET area is only 250 $m^2/g$ lower than the theoretical value. It is speculated, without wishing to be bound by theory, that this might be because of pore blocking effects.

TABLE 3

BET areas of different MOFs and MOF-ZIF8 composites

| Material | $S_{BET}$ $m^2/g$ |
|---|---|
| ZIF-8LT | 1387 |
| UiO-66 | 1173 |
| MIL-101 | 2426 |
| ZIF-90 | 1036 |
| UiO-66@ZIF-8 | 710 |
| MIL-101@ZIF-8 | 1455 |
| ZIF-90@ZIF-8 | 946 |

Table 4 shows the mechanical properties of UiO-6@ZIF8 and MIL-101@ZIF-8. Both the elastic modulus (E) and hardness (H) of the MOF@ZIF-8 composites are of the same order as those of ZIF-8ER.

TABLE 4

Mechanical properties of different MOF-ZIF8 composite and ZIF-8-ER with indentation depth of 500 nm.

| Materials | Elastic modulus (E) GPa | Hardness (H) GPa |
|---|---|---|
| ZIF-8ER | 7.04 ± 0.13 | 0.643 ± 0.021 |
| UiO-66@ZIF-8 | 6.864 ± 0.498 | 0.490 ± 0.052 |
| MIL-101@ZIF-8 | 6.915 ± 0.394 | 0.531 ± 0.046 |

Measurement of Porosity and BET Specific Surface Area by $N_2$ Adsorption $N_2$ adsorption isotherms were recorded at 77 K using a Micromeritics ASAP 2020 instrument. Prior to the measurements, the samples were degassed at 425 K using a heating rate of 5 K $min^{-1}$ for 4 h.

The BET equation was applied to experimental $N_2$ isotherms using the consistency criteria suggested in the literature and carefully assuring that the BET constant remains positive [Rouquerol et al (1999)]. In the experimental isotherm, the BET equation was fitted over a broad range of pressures.

Nanoindentation

Nanoindentation experiments were performed using an MTS Nanoindenter XP, located in an isolation cabinet to shield against thermal fluctuations and acoustic interference.

Before indentation, monolith surfaces were first cold-mounted using an epoxy resin and then carefully polished using increasingly fine diamond suspensions. Indentations were conducted under the dynamic displacement-controlled "continuous stiffness measurement" mode. E (Elastic modulus) and H (Hardness) mechanical properties were subsequently determined as a function of the surface penetration depth. A 2-nm sinusoidal displacement at 45 Hz was superimposed onto the system's primary loading signal, and the loading and unloading strain rates were set at $5 \times 10^{-2}$ s$^{-1}$. All tests were performed to a maximum indentation depth of 1,000 nm using a Berkovich (i.e. three-sided pyramidal) diamond tip of radius about 100 nm. The raw data (load-displacement curves) obtained were analysed using the Oliver and Pharr (2004) method, and Poisson's ratio set at 0.2, in accordance with prior work on zeolitic imidazolate frameworks [Tan et al (2010)]. Data resulting from surface penetrations of less than 100 nm were discarded due to imperfect tip-surface contacts.

Figure 12:
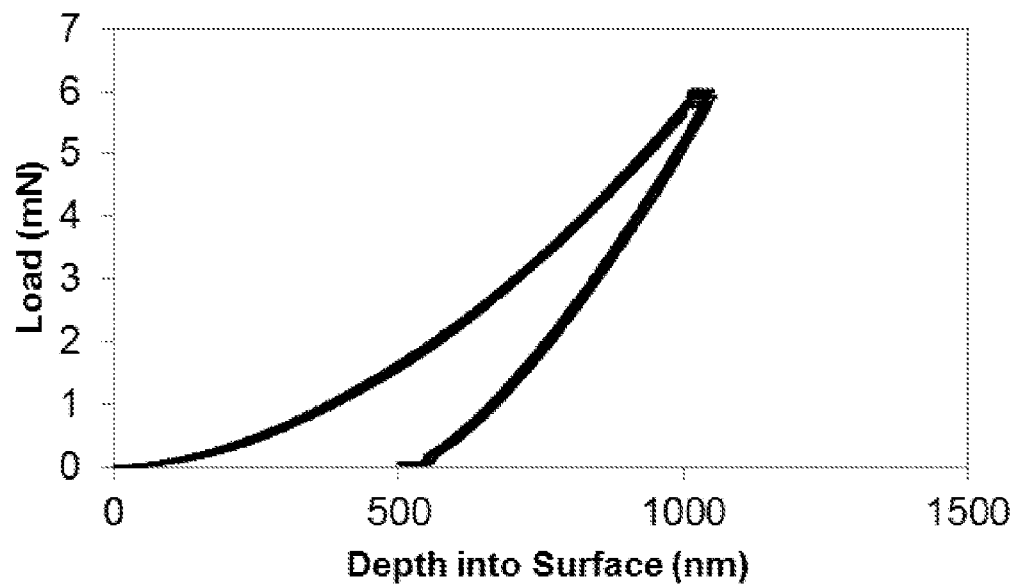
FIG. 12 shows 10 overlaid load-depth curves for nanoindentation of a ZIF-8-LT sample.
Figure 13:
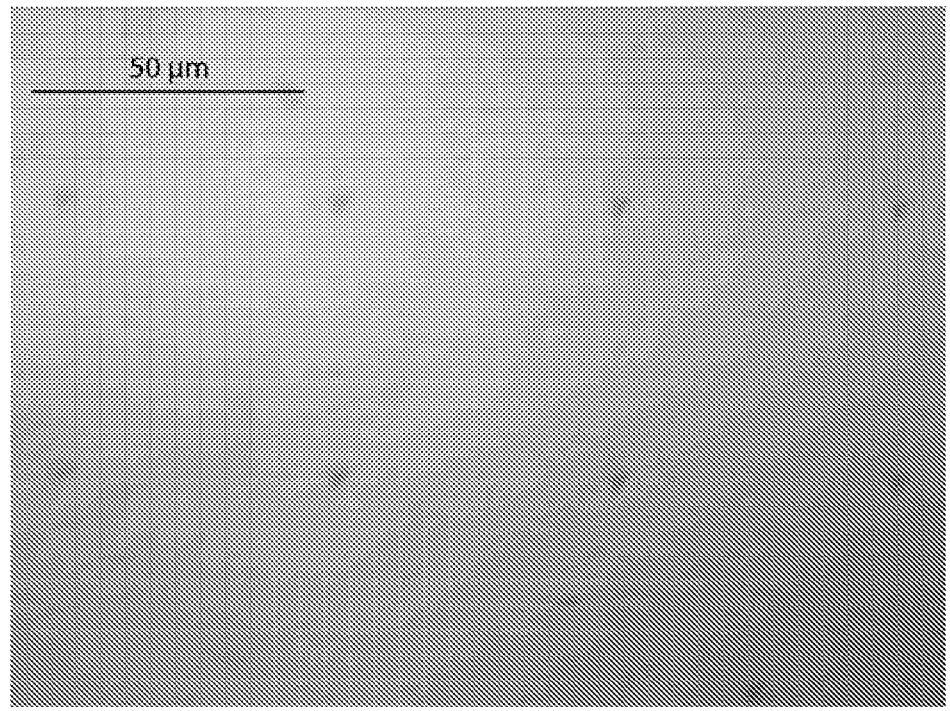
FIG. 13 shows an SEM image of two rows of 1000 nm indents made on a sample (5×5 mm) of ZIF-8-LT.
Figure 14:
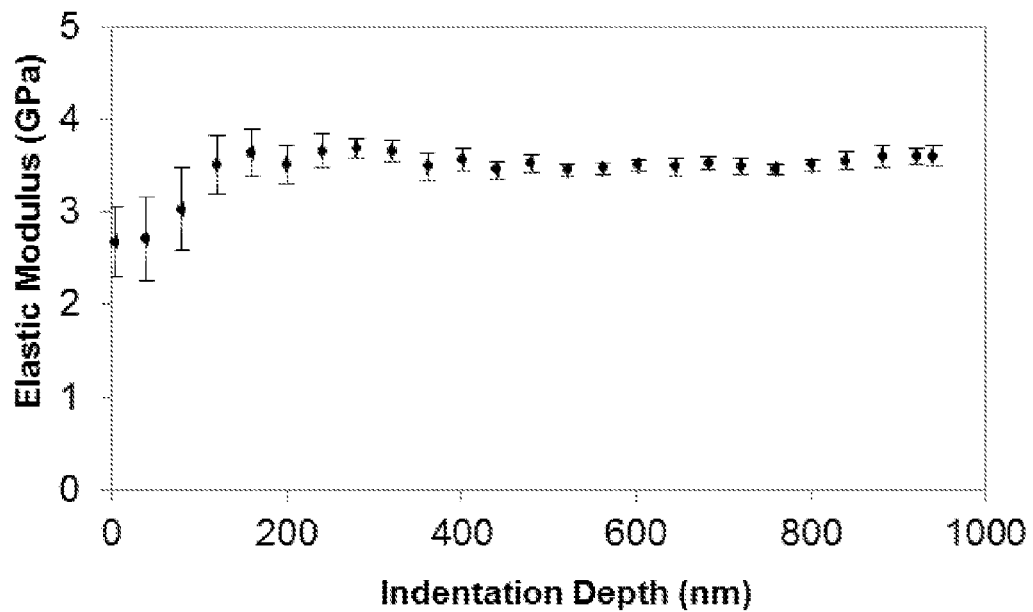
FIG. 14 shows results for the elastic modulus of ZIF-8LT as a function of indentation depth.
Figure 15:
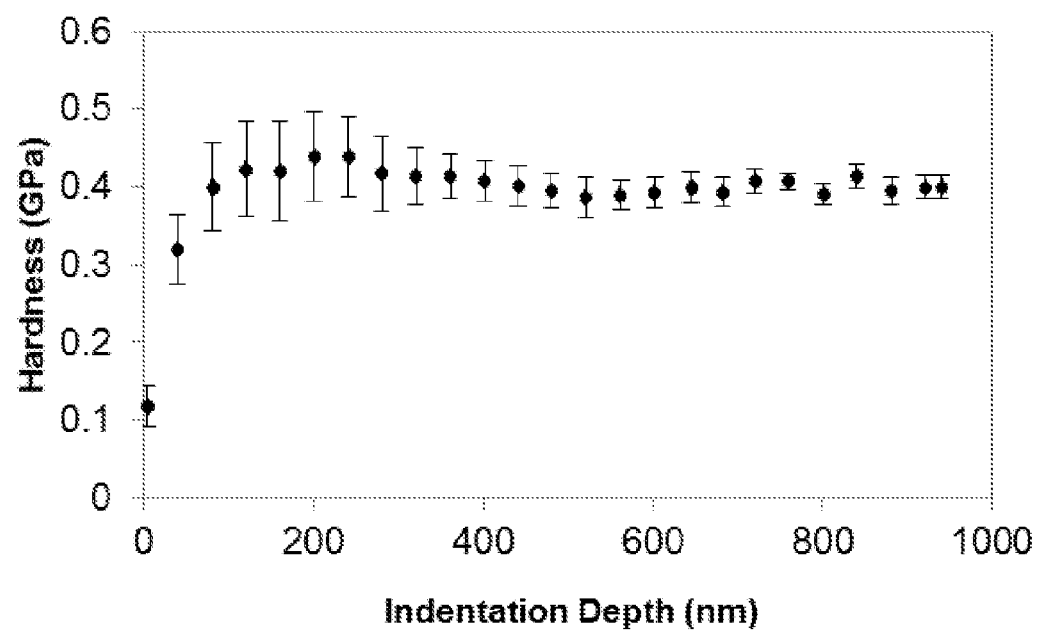
FIG. 15 shows results for the hardness of ZIF-8LT as a function of indentation depth.

For ZIF-8LT, 45 indents of 1000 nm were performed. For illustration, 10 overlaid load-depth curves are shown in FIG. 12, showing the consistency of behaviour for the ZIF-8LT sample. FIG. 13 shows an SEM image of two rows of 1000 nm indents made on a sample (5×5 mm) of ZIF-8LT. FIG. 14 shows results for the elastic modulus of ZIF-8LT as a function of indentation depth. FIG. 15 shows results for the hardness of ZIF-8LT as a function of indentation depth. In each of FIGS. 14 and 15, each error bar arises from the standard deviation of 45 indents.

Figure 16:
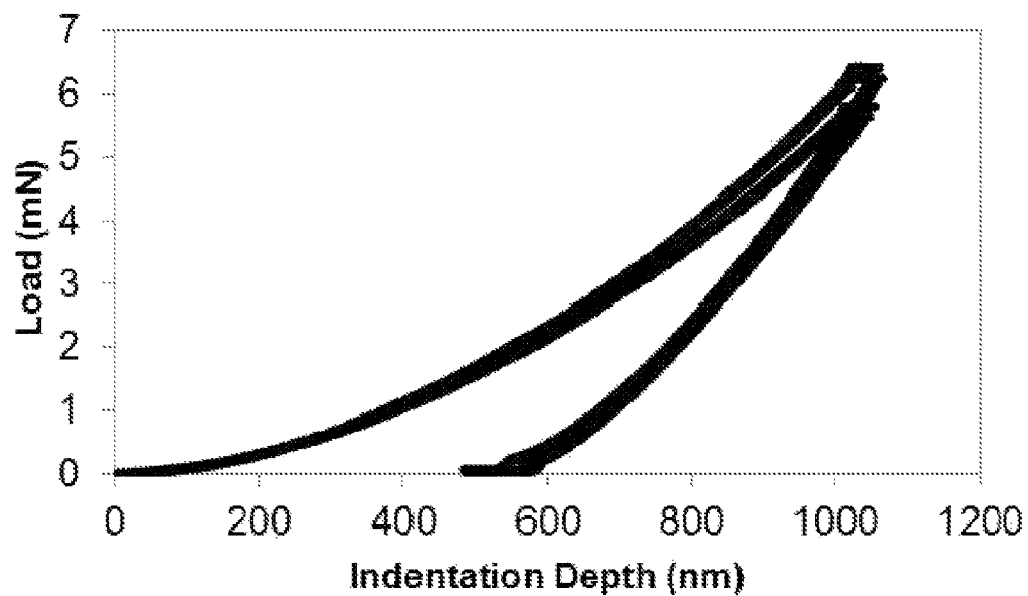
FIG. 16 shows 20 overlaid load-depth curves for the ZIF-8-LTHT sample.
Figure 17:
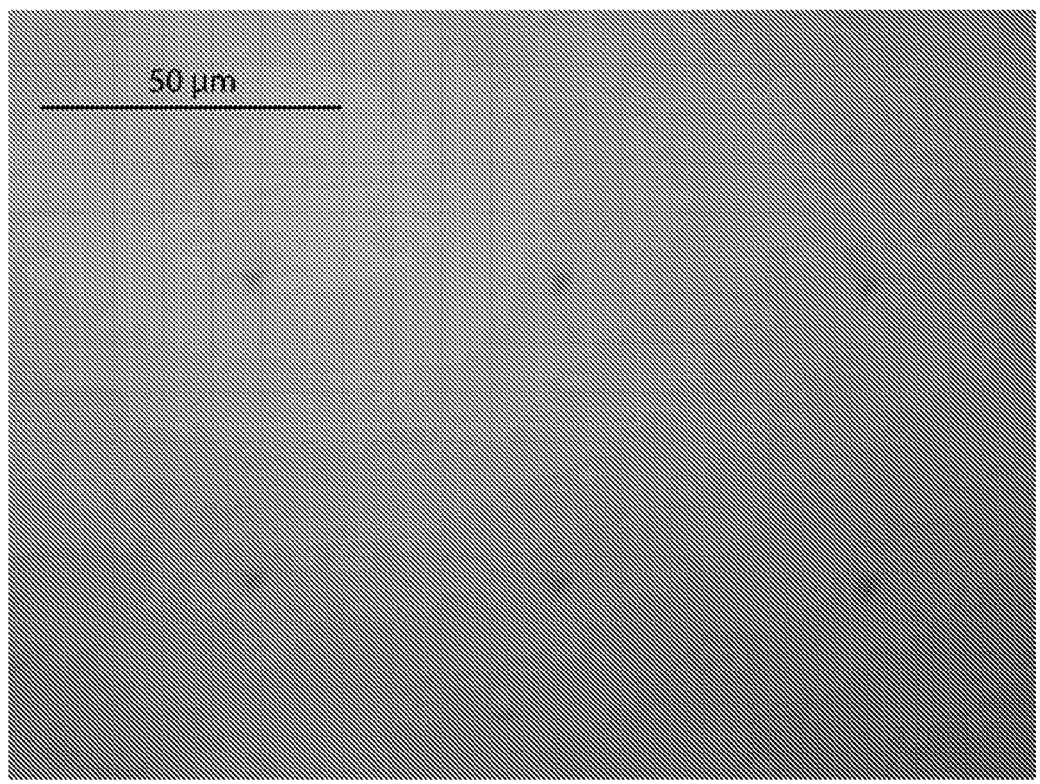
FIG. 17 shows an SEM image of two rows of 1000 nm indents made on a sample (5×5 mm) of ZIF-8-LTHT.
Figure 18:
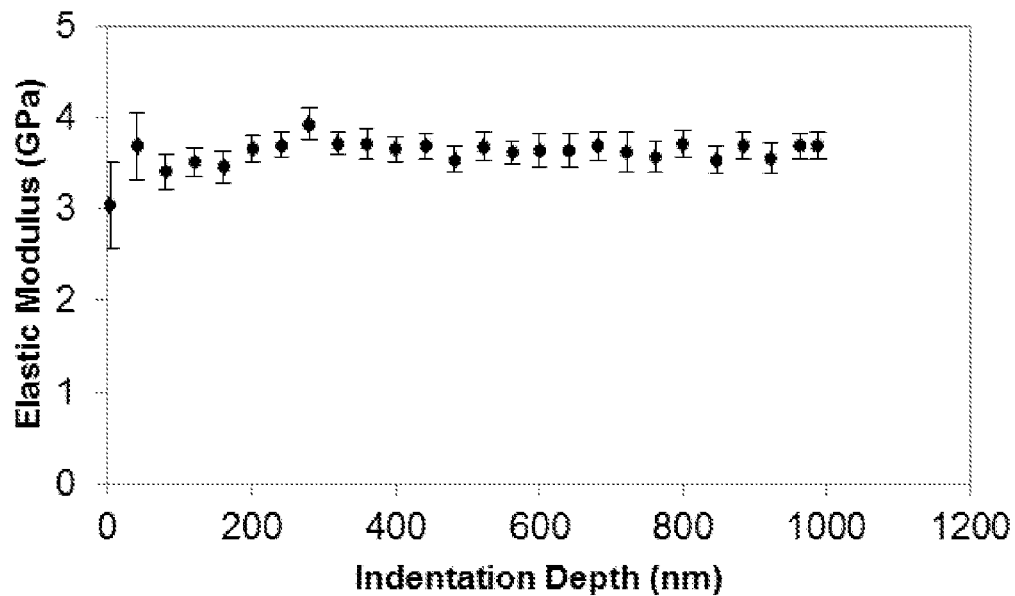
FIG. 18 shows results for the elastic modulus of ZIF-8-LTHT as a function of indentation depth.
Figure 19:
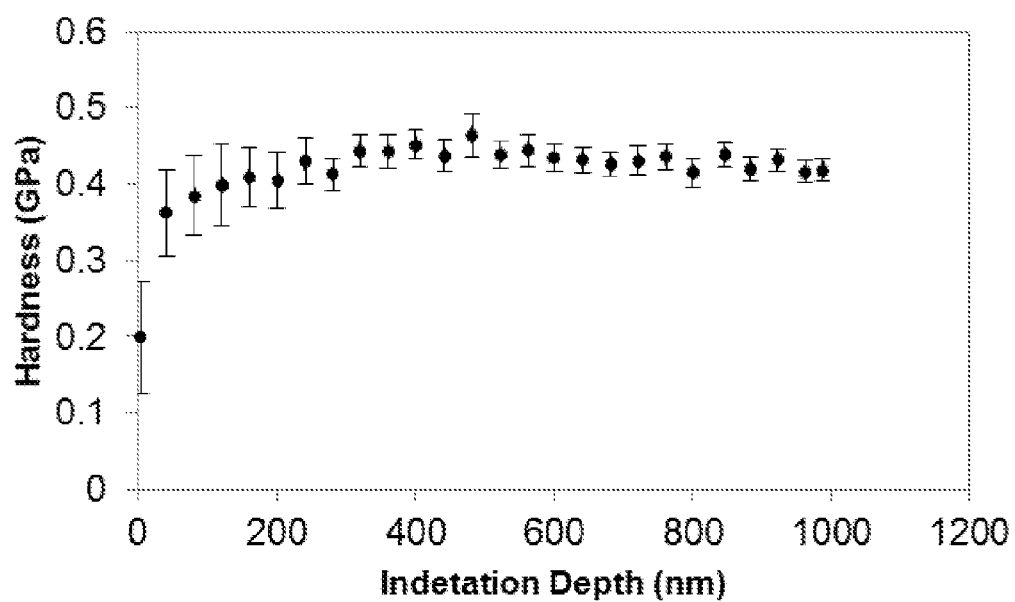
FIG. 19 shows results for the hardness of ZIF-8-LTHT as a function of indentation depth.

FIG. 16 shows 20 overlaid load-depth curves for the ZIF-8LTHT sample. FIG. 17 shows an SEM image of two rows of 1000 nm indents made on a sample (5×5 mm) of ZIF-8LTHT. FIG. 18 shows results for the elastic modulus of ZIF-8LTHT as a function of indentation depth. FIG. 19 shows results for the hardness of ZIF-8LTHT as a function of indentation depth. In each of FIGS. 18 and 19, each error bar arises from the standard deviation of 45 indents.

For ZIF-8-ER, two nanoindentation analyses were carried out. In the first, a monolith of ZIF-8ER was subjected to 6 indents of depth 3000 nm. In the second, another monolith of ZIF-8ER was subjected to 15 indents of depth 1000 nm.

Figure 20:
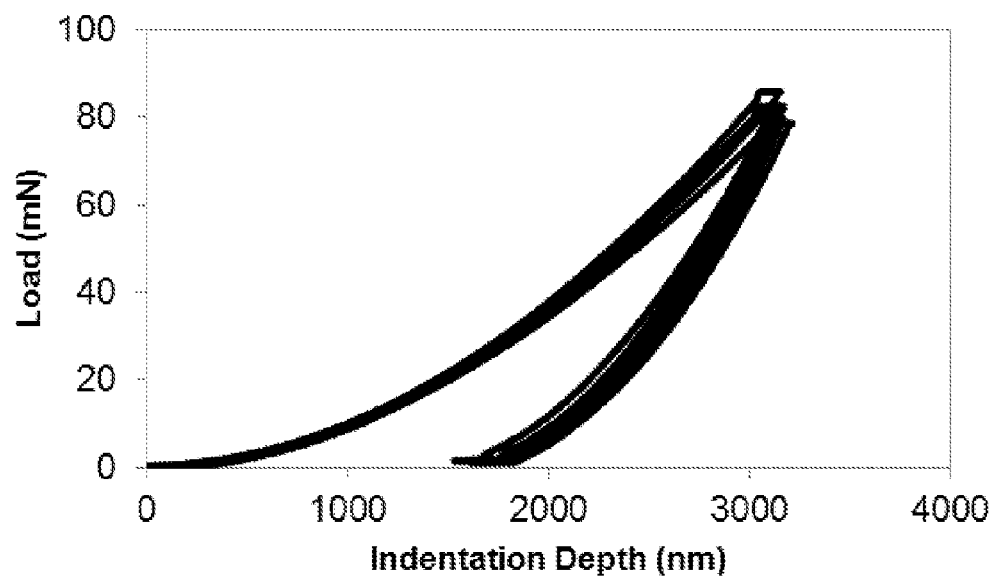
FIG. 20 shows 6 overlaid load-depth curves for the ZIF-8-ER sample indented to 3000 nm.
Figure 21:
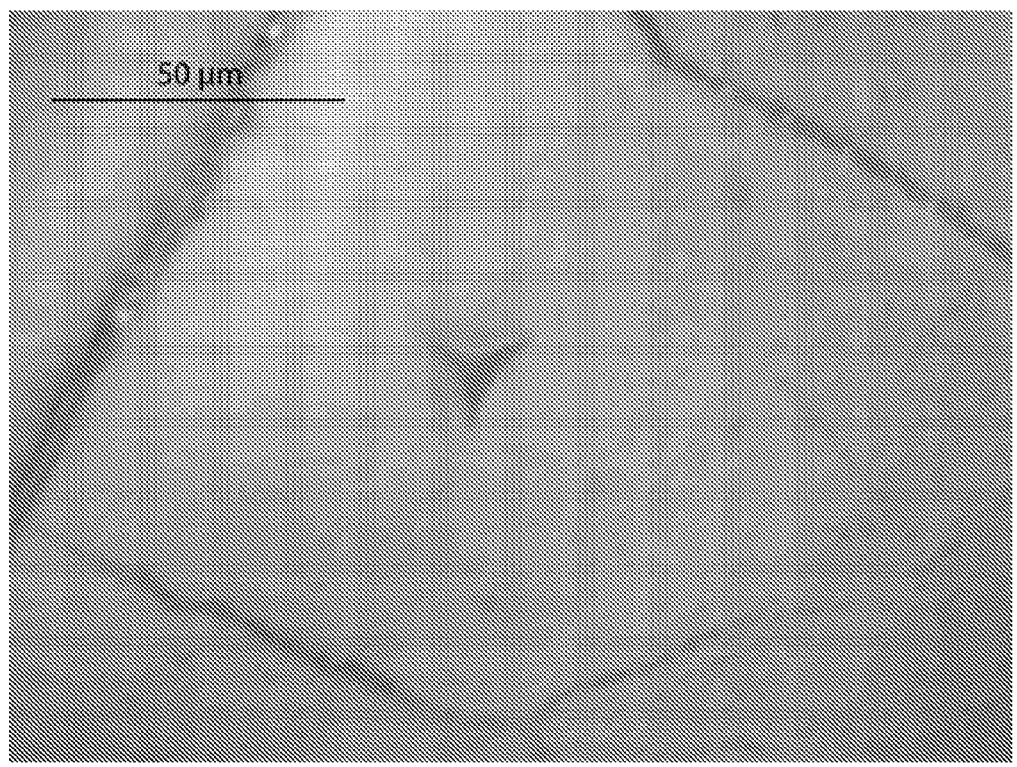
FIG. 21 shows a 3000 nm indent made on a sample (5×5 mm) of ZIF-8-ER.
Figure 22:
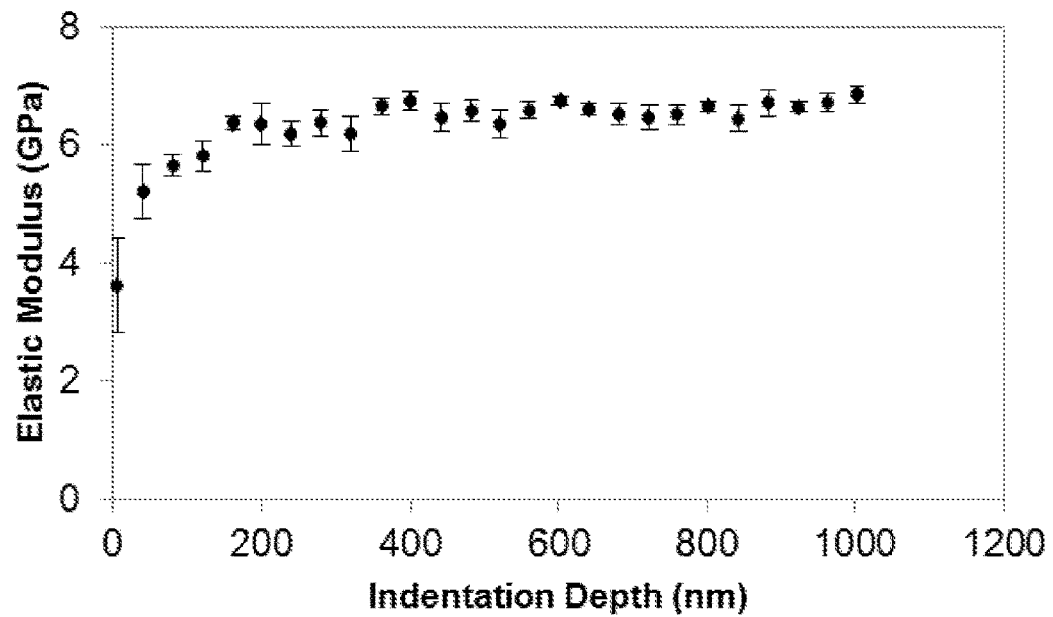
FIG. 22 shows results for the elastic modulus of ZIF-8-ER as a function of indentation depth.
Figure 23:
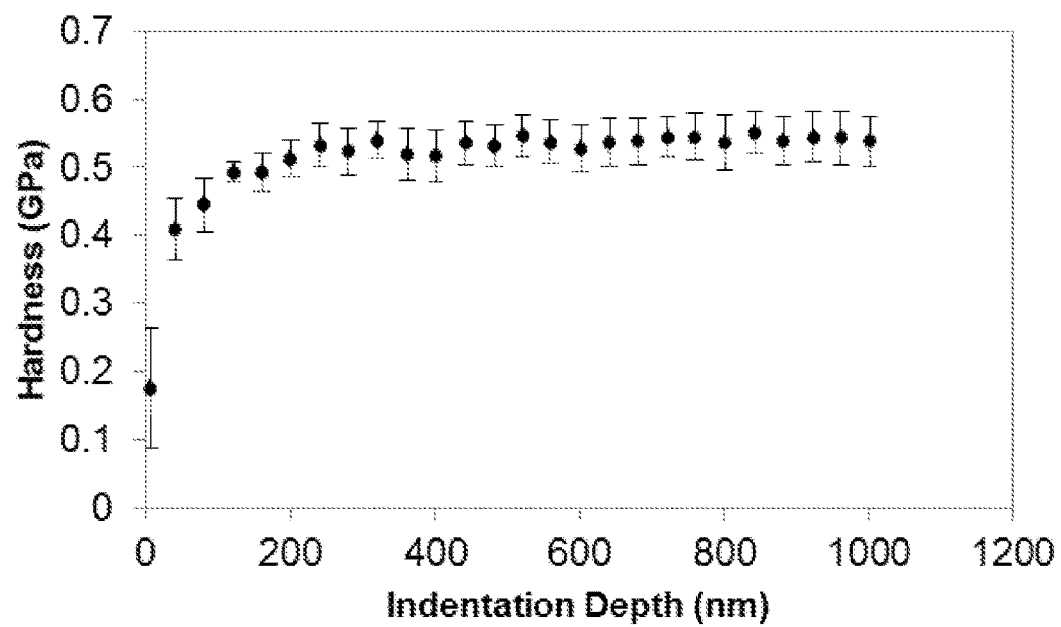
FIG. 23 shows results for the hardness of ZIF-8-ER as a function of indentation depth.

FIG. 20 shows 6 overlaid load-depth curves for the ZIF-8ER sample indented to 3000 nm. FIG. 21 shows a 3000 nm indent made on a sample (5×5 mm) of ZIF-8ER. FIG. 22 shows results for the elastic modulus of ZIF-8ER as a function of indentation depth. FIG. 23 shows results for the hardness of ZIF-8ER as a function of indentation depth. In each of FIGS. 22 and 23, each error bar arises from the standard deviation of 6 indents.

Figure 24:
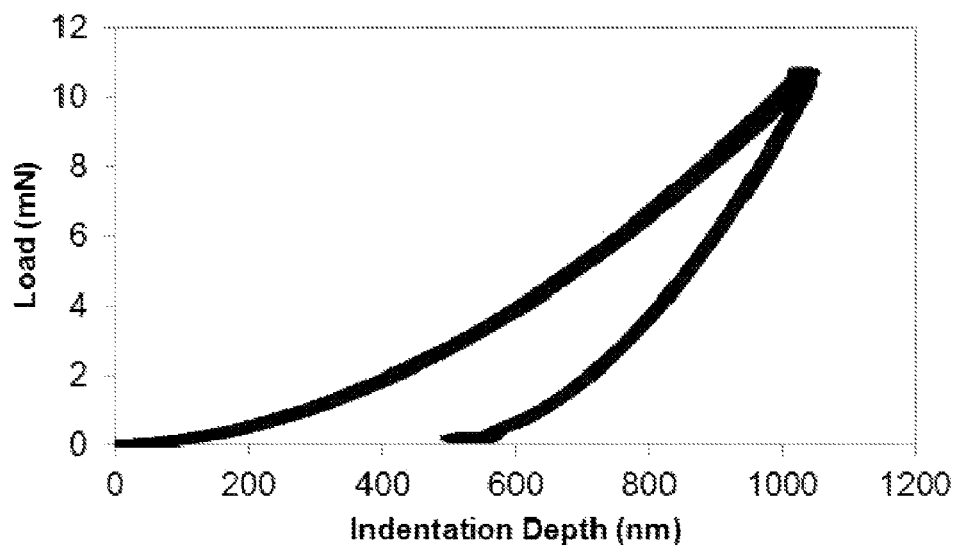
FIG. 24 shows 15 overlaid load-depth curves for the ZIF-8-ER sample indented to 1000 nm.
Figure 25:
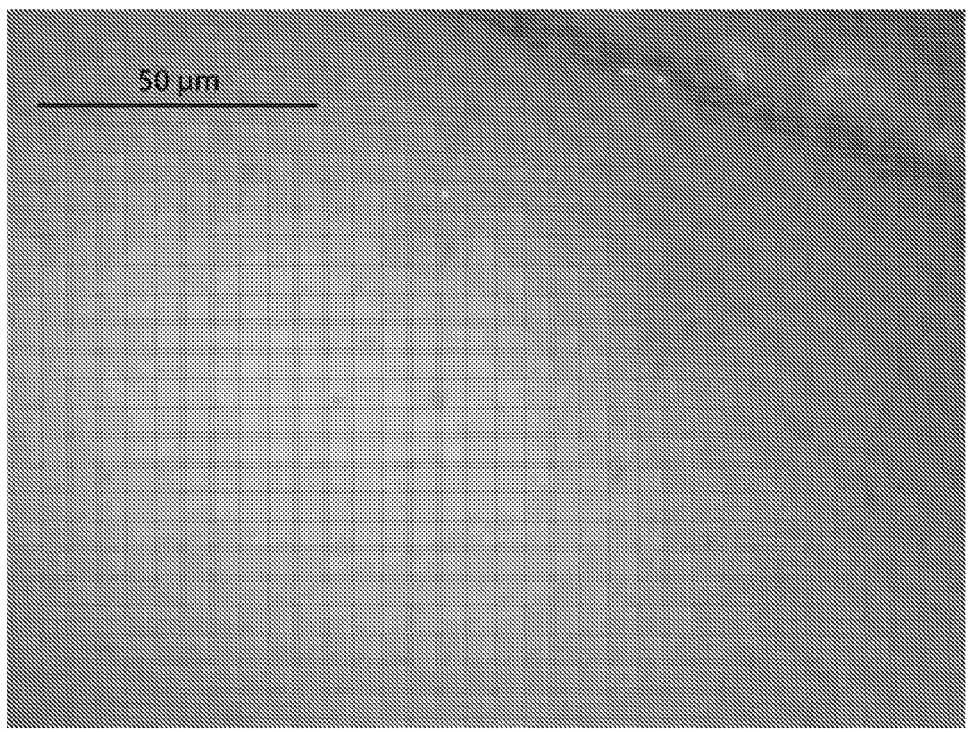
FIG. 25 shows rows of 1000 nm indents made on a sample (5×5 mm) of ZIF-8-ER.
Figure 26:
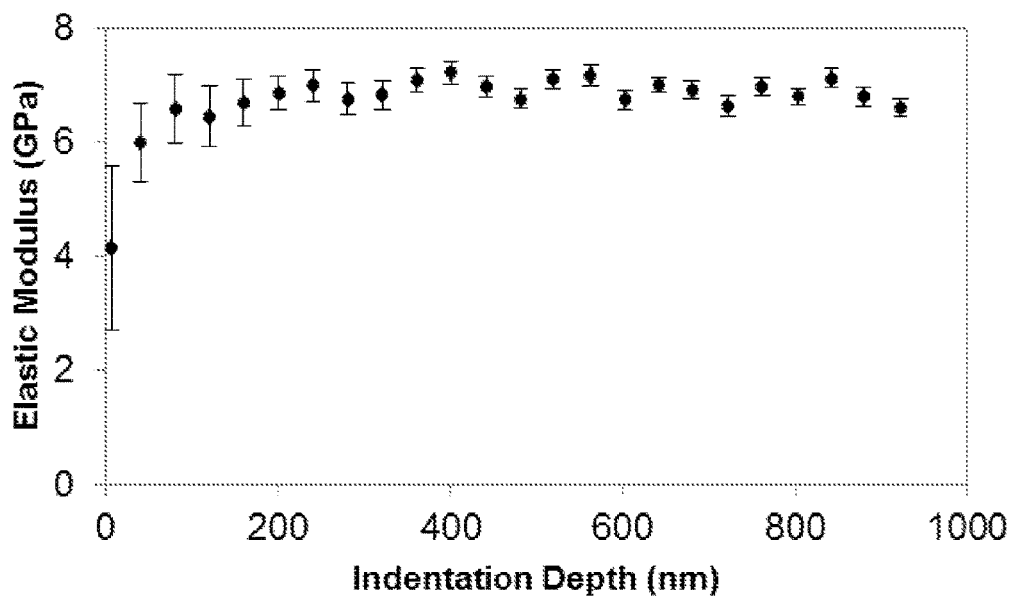
FIG. 26 shows results for the elastic modulus of ZIF-8-ER as a function of indentation depth.
Figure 27:
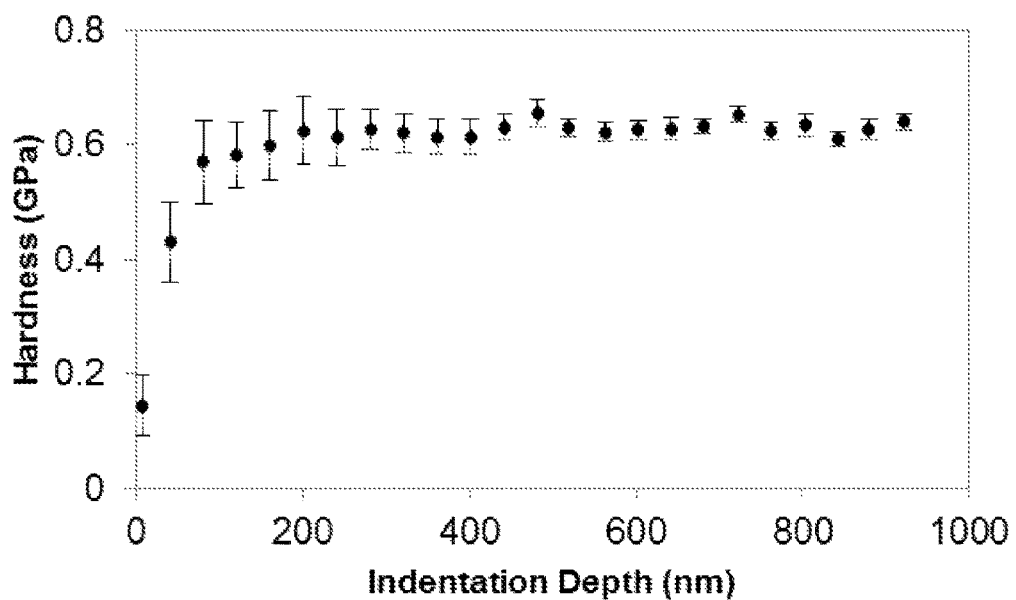
FIG. 27 shows results for the hardness of ZIF-8-ER as a function of indentation depth.

FIG. 24 shows 15 overlaid load-depth curves for the ZIF-8ER sample indented to 1000 nm. FIG. 25 shows rows of 1000 nm indents made on a sample (5×5 mm) of ZIF-8ER. FIG. 26 shows results for the elastic modulus of ZIF-8ER as a function of indentation depth. FIG. 27 shows results for the hardness of ZIF-8ER as a function of indentation depth. In each of FIGS. 26 and 27, each error bar arises from the standard deviation of 15 indents.

Further Experimental Details

Powder X-ray diffraction (XRD) patterns were recorded with a Bruker D8 diffractometer using CuK$\alpha_1$ ($\lambda$=1.5405 Å$^{-1}$) radiation with a step of 0.02° at a scanning speed of 0.1° s$^{-1}$.

Scanning electron microscope (SEM) images were taken by FEI XL30 FEGSEM with an accelerating voltage of 5 kV.

Figure 11:
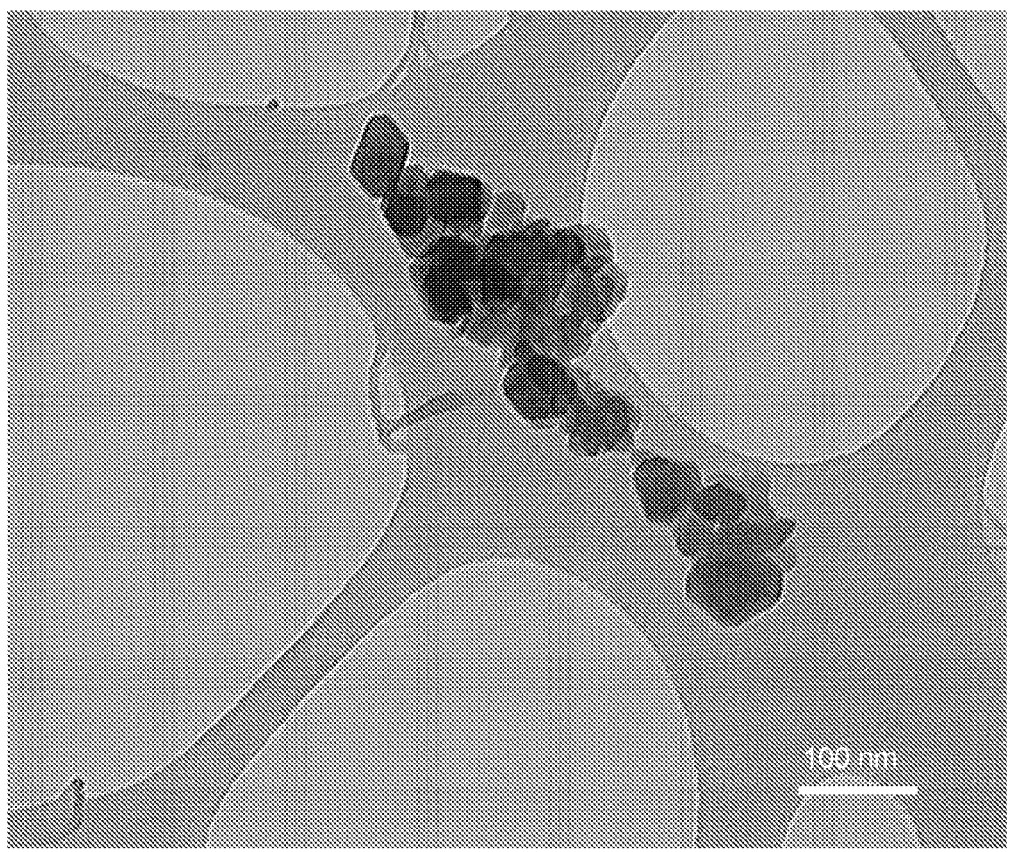
FIG. 11 shows a TEM image of ZIF-8-LT.

TEM images were obtained using a FEI Tecnai G2 with a 200 kV voltage. 1 ml of the mother solution was taken and diluted 10 times by ethanol before centrifugation. 50 μl of the solution was dripped on a copper grid. The TEM image shown in FIG. 11 was taken after the ethanol evaporated at room temperature.

Thermogravimetric analysis (TGA) was performed using a Pyris 1 TGA under N$_2$ atmosphere, from room temperature to 750° C., using a ramp rate of 10° C. min$^{-1}$.

Figure 28:
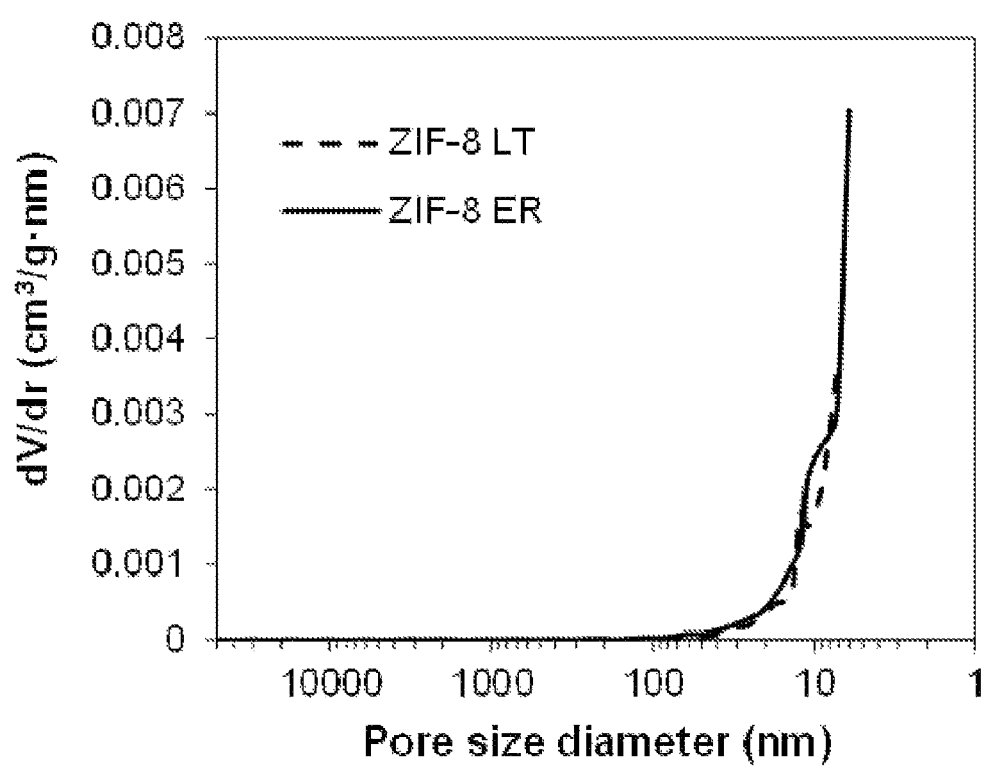
FIG. 28 shows the results of mercury porosimetry showing pore size distribution of the macro- and mesoporosity of ZIF-8-LT and ZIF-8-ER.

Mercury porosimetry was obtained up to a final pressure of 2000 bar using an AutoPore IV 9500 instrument. With this technique, the volume of the pores greater than 100 nm and the bulk particle density at atmospheric pressure were obtained. FIG. 28 shows the results of mercury porosimetry showing pore size distribution of the macro- and mesoporosity of ZIF-8LT and ZIF-8ER.

The chemical stability of ZIF-8ER was tested in refluxing water at 100° C. for seven days. The stability was monitored using XRD every 48 hours from day 3.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

All references referred to above are hereby incorporated by reference.

LIST OF NON-PATENT DOCUMENT REFERENCES

J. Rouquerol, D. Avnir, C. W. Fairbridge, D. H. Everett, J. H. Haynes, N. Pernicone, J. D. F. Ramsay, K. S. W. Sing, and K. K. Unger *Pure and Applied Chemistry*, vol. 66, p. 1739, 1994.

K. S. W. Sing *Pure & Appl. Chem.*, 4, 11, 2201-2218, 1982.

S. Cao, G. Gody, W. Zhao, S. Perrier, X. Peng, C. Ducati, D. Zhao and A. K. Cheetham *Chem. Sci.*, 2013, 4, 3573-3577

K. S. Park, Z. Ni, A. P. Côté, J. Y. Choi, R. Huang, F. J. Uribe-Romo, H. K. Chae, M. O'Keeffe, and O. M. Yaghi, *Proc. Natl. Acad. Sci. U.S.A*, 2006, 103, 10186-91.

Y.-Q. Tian, Y.-M. Zhao, Z.-X. Chen, G.-N. Zhang, L.-H. Weng, and D.-Y. Zhao, *Chemistry*, 2007, 13, 4146-54.

H. Furukawa, K. E. Cordova, M. O'Keeffe, and O. M. Yaghi, *Science*, 2013, 341, 1230444.

T. D. Bennett, P. J. Saines, D. A. Keen, J.-C. Tan, and A. K. Cheetham, *Chemistry*, 2013, 19, 7049-55.

K. W. Chapman, G. J. Halder, and P. J. Chupas, *J. Am. Chem. Soc.*, 2009, 131, 17546-7.

Y.-Y. Fu, C.-X. Yang, and X.-P. Yan, *Chem. Commun.*, 2013, 49, 7162-4.

Hsi-Ya Huang, Cheng-Lan Lin, Cheng-You Wu, Yi-Jie Cheng, Chia-Her Lin *Analytica Chimica Acta* Volume 779, 2013, Pages 96-103

P. Küsgens, A. Zgaverdea, H.-G. Fritz, S. Siegle, and S. Kaskel, *J. Am. Ceram. Soc.*, 2010, 93, 2476-2479.

D. Fairen-Jimenez, S. Moggach, M. T. Wharmby, P. Wright, S. Parsons and T. Düren, *J. Am. Chem. Soc.*, 2011, 133, 8900-2.

David Fairen-Jimenez, Raimondas Galvelis, Antonio Torrisi, Alistair D. Gellan, Michael T. Wharmby, Paul A. Wright, Caroline Mellot-Draznieks and Tina Düren *Dalton Transactions* Issue 35, 2012

M. R. Lohe, M. Rose, and S. Kaskel, *Chem. Commun.,* 2009, 6056-8.

L. Li, S. Xiang, S. Cao, J. Zhang, G. Ouyang, L. Chen, and C.-Y. Su, *Nat. Commun.,* 2013, 4, 1774.

D. Fairén-Jimenez, F. Carrasco-Marin, and C. Moreno-Castilla, *Langmuir,* 2008, 24, 2820-5.

D. Fairén-Jiménez, F. Carrasco-Marin, C. Moreno-Castilla *Carbon* Volume 44, Issue 11, September 2006, Pages 2301-2307

J. C. Tan, T. D. Bennett, and A. K. Cheetham, PNAS 2010, 107, 22, 9938-9943.

D. Fairén-Jiménez, F. Carrasco-Marin, D. Djurado, F. Bley, F. Ehrburger-Dolle, and C. Moreno-Castilla, *J. Phys. Chem. B,* 2006, 110, 8681-8.

R. Apetz and M. P. B. Bruggen, *J. Am. Ceram. Soc.,* 2003, 86, 480-486.

S. Eslava, L. Zhang, S. Esconjauregui, J. Yang, K. Vanstreels, M. R. Baklanov, and E. Saiz, *Chem. Mater.,* 2013, 25, 27-33.

S. Bundschuh, O. Kraft, H. K. Arslan, H. Gliemann, P. G. Weidler, and C. Wöll, *Appl. Phys. Lett.,* 2012, 101, 101910.

Q. Song, S. K. Nataraj, M. V. Roussenova, J. C. Tan, D. J. Hughes, W. Li, P. Bourgoin, M. A. Alam, A. K. Cheetham, S. A. Al-Muhtaseb, and E. Sivaniah, *Energy Environ. Sci.,* 2012, 5, 8359.

J. Juan-Juan, J. P. Marco-Lozar, F. Suarez-Garcia, D. Cazorla-Amorós, and A. Linares-Solano, *Carbon,* 2010, 48, 2906-2909.

Rouquerol, J.; Rouquerol, F.; Sing, K. S. W., *Adsorption by powders and porous solids* Academic Press: San Diego, 1999.

W. C. Oliver and G. M. Pharr, *J Mater Res,* 2004, 19, 3-20.

D. Fairen-Jimenez, R. Galvelis, A. Torrisi, A. D. Gellan, M. T. Wharmby, P. a Wright, C. Mellot-Draznieks, and T. Düren, Dalton Trans., 2012, 41, 10752-62.

M. J. Katz, Z. J. Brown, Y. J. Colon, P. W. Siu, K. a Scheidt, R. Q. Snurr, J. T. Hupp, and O. K. Farha, Chem. Commun., 2013, 49, 9449-51.

N. A. Khan, I. J. Kang, H. Y. Seok, and S. H. Jhung, Chem. Eng. J., 2011, 166, 1152-1157.

F.-K. Shieh, S.-C. Wang, S.-Y. Leo, and K. C.-W. Wu, Chem. Eur. J., 2013, 19, 11139-42.

R. Zacharia, D. Cossement, L. La. and R. Chahine, J. Mater. Chem., 2010, 20, 2145.

The invention claimed is:

1. A metal-organic framework (MOF) body comprising MOF crystallites adhered to each other via a binder comprising MOF.

2. A metal-organic framework (MOF) body consisting of:
    MOF crystallites;
    a binder comprising MOF which binds the crystallites together in the body;
    optionally, residual solvent; and
    optionally, one or more additives, wherein the additives are present at a level of not more than 10% by mass.

3. The MOF body according to claim 1 wherein the body is a monolith.

4. The MOF body according to claim 3 wherein the body has a volume of at least 1 mm$^3$.

5. The MOF body according to claim 3 wherein the body is a monolith having a volume of at least 10 mm$^3$.

6. The MOF body according to claim 1 wherein the body is a layer formed on a substrate.

7. The MOF body according to claim 1 wherein the binder comprising MOF has substantially the same composition as the MOF crystallites.

8. The MOF body according to claim 1 wherein the binder comprising MOF has a different composition to the MOF crystallites.

9. The MOF body according to claim 1 wherein:
    (i) when the body is formed from a composition capable of forming a MOF single crystal of the same composition, the density of the MOF body is at least 90% of the density of a MOF single crystal of the same composition; or
    (ii) when the body is formed from a composition not capable of forming a single crystal of the same composition, instead being capable of forming a MOF single crystal and one or more remaining components of the composition, the density of the MOF body is at least 90% of the volumetric weighted arithmetic mean of the density of said MOF single crystal and said remaining component.

10. The MOF body according to claim 9 wherein the density of the MOF body is at least 105% of:
    (i) the density of the MOF single crystal of the same composition, or
    (ii) the volumetric weighted arithmetic mean of the density of said MOF single crystal and said remaining components.

11. A metal-organic framework (MOF) monolith having a volume of at least 1 mm$^3$, wherein:
    (i) when the monolith is formed from a composition capable of forming a MOF single crystal of the same composition, the BET surface area per unit bulk volume of the monolith is at least 0.6 times the BET surface area per unit bulk volume of said MOF single crystal of the same composition; and
    (ii) when the monolith is formed from a composition not capable of forming a single crystal of the same composition, instead being capable of forming a MOF single crystal and one or more remaining components of the composition, the BET surface area per unit bulk volume of the monolith is at least 0.6 times the volumetric weighted arithmetic mean of the BET surface area per unit bulk volume of said MOF single crystal and said remaining components,
    and wherein the BET surface area per unit bulk volume is determined based on the $N_2$ adsorption isotherm at 77K.

12. The MOF monolith according to claim 11 having a volume of at least 10 mm$^3$.

13. The MOF monolith according to claim 11 wherein the BET surface area per unit bulk volume of the monolith is at least 600 m$^2$/cm$^3$.

14. The MOF monolith according to claim 11 having a meso-porosity of at most 10 vol %, wherein meso-porosity is defined as pores with diameter in the range 2-50 nm (macro-porosity being defined as pores of greater than 50 nm diameter), the porosity and pore size distributions being determined based on the $N_2$ adsorption isotherm at 77K.

15. The MOF monolith according to claim 11 having a micro-porosity, defined as pores with diameter less than 2 nm, of at least 40 vol %.

16. The MOF body according to claim 11 having a volume of at least 100 mm$^3$.

17. The MOF body according to claim 11 having a smallest linear dimension of at least 1 mm.

18. A population of metal-organic framework (MOF) monoliths each having a volume of at least 1 mm$^3$, wherein, for each monolith:
    (i) when the monolith is formed from a composition capable of forming a MOF single crystal of the same composition, the BET surface area per unit bulk volume of the monolith is at least 0.6 times the BET surface area per unit bulk volume of said MOF single crystal of the same composition; and (ii) when the monolith is formed from a composition not capable of forming a single crystal of the same composition, instead being capable of forming a MOF single crystal and one or more remaining components of the composition, the BET surface area per unit bulk volume of the monolith is at least 0.6 times the volumetric weighted arithmetic mean of the BET surface area per unit bulk volume of said MOF single crystal and said remaining components, and wherein the BET surface area per unit bulk volume is determined based on the $N_2$ adsorption isotherm at 77K.

* * * * *